(12) United States Patent
Tam et al.

(10) Patent No.: US 8,452,543 B2
(45) Date of Patent: May 28, 2013

(54) HIGH THROUGHPUT SCREENING FOR ANTIMICROBIAL DOSING REGIMENS

(75) Inventors: Vincent H. Tam, Bellaire, TX (US); Michael Nikolaou, Houston, TX (US)

(73) Assignee: The University of Houston System, Houston, TX (US)

( * ) Notice: Subject to any disclaimer, the term of this patent is extended or adjusted under 35 U.S.C. 154(b) by 681 days.

(21) Appl. No.: 11/992,633

(22) PCT Filed: Sep. 19, 2006

(86) PCT No.: PCT/US2006/036458
§ 371 (c)(1),
(2), (4) Date: Jul. 1, 2010

(87) PCT Pub. No.: WO2007/035719
PCT Pub. Date: Mar. 29, 2007

(65) Prior Publication Data
US 2010/0292964 A1    Nov. 18, 2010

Related U.S. Application Data

(60) Provisional application No. 60/718,463, filed on Sep. 19, 2005.

(51) Int. Cl.
G06F 19/10    (2011.01)
G06G 7/58    (2006.01)

(52) U.S. Cl.
USPC ............................................. 702/19; 703/11

(58) Field of Classification Search
None
See application file for complete search history.

(56) References Cited

U.S. PATENT DOCUMENTS
2003/0190603 A1    10/2003  Larder ............................. 435/5

OTHER PUBLICATIONS

Tam, V. et al. A Novel Approach to Pharmacodynamic Assessment of Antimicrobial Agents: New Insights to Dosing Regimen Design: *PLoS Computational Biology*, Jan. 2011, vol. 7, No. 1, pp. 1-8.

Nikolaou, M. et al. A New Modeling Approach to the Effect of Antimicrobial Agents on Heterogeneous Microbial Populations: *Journal Mathematical Biology*, 2005.
Tam, V. et al. Modelling Time-kill Studies to Discern the Pharmacodynamics of Meropenem: *Journal of Antimicrobial Chemotherapy*, 2005, vol. 55, pp. 699-706.
Nikolaou, M. et al. Modeling of Microbial Population Responses to Time-Periodic Concentrations of Antimicrobial Agents: *Annals. of Biomedical Engineering*, Aug. 2007, vol. 35, No. 8, pp. 1458-1470.
Tam, V. et al. Mathematical Modelling Response of Pseudomonas aeruginosa to Meropenem: *Journal Antimicrobial Chemotherapy*, 2007, vol. 60, pp. 1302-1309.
Bhagunde, P. et al. Mathematical Modelling to Characterize the Inoculum Effect: *Antimicrobial Agents and Chemotherapy*, 2010, vol. 54, No. 11, pp. 4739-4743.
Tam, V. et al. Pharmacodynamic Modeling of Aminoglycosides Against Pseudomonas aeruginosa and Acinetobacter baumannii: Identifying Dosing Regimens to Suppress Resistance Development: *Antimicrobial Agents and Chemotherapy*, Nov. 2008, pp. 3987-3993.
Gumbo, T. et al. Selection of a Moxifloxacin Dose That Suppresses Drug Resistance in Mycobacterium tuberculosis, by Use of an In Vitro Pharmacodynamic Infection Model and Mathematical Modeling: *Journal of Infectious Diseases*, Nov. 1, 2004, vol. 190, pp. 1642-1651.
Christopher, R. et al. Data-Driven Computer Simulation of Human Cancer Cell: *Annals. of the New York Academy of Science*: 2004, vol. 1020, pp. 132-153.
Kuczek, T. et al. Mechanism-Based Model for Tumor Drug Resistance; *Cancer Chemotherapy and Pharmacology*: 1992, vol. 30, pp. 355-359.

*Primary Examiner* — Lori A. Clow
(74) *Attorney, Agent, or Firm* — Benjamin Aaron Adler

(57) ABSTRACT

Provided herein are methods and computer-implemented systems for using computer simulations to predict likelihood of a cell population associated with a pathophysiological condition acquiring resistance to a therapeutic agent, to screen for therapeutic agents effective to suppress acquisition of resistance within a cell population and to treat the pathophysiological conditions associated therewith. The computer simulation comprises at least an input/out system and a mathematical model, including operably linked equations, parameter values and constant values, of growth response over a period of time of a cell population in contact with an therapeutic agent. Also provide is a method for determining a best-fit mathematical model of adaptation of a microbial population to a therapeutic agent over time and using the model to simulate microbial population behavior to a therapeutic agent.

6 Claims, 24 Drawing Sheets

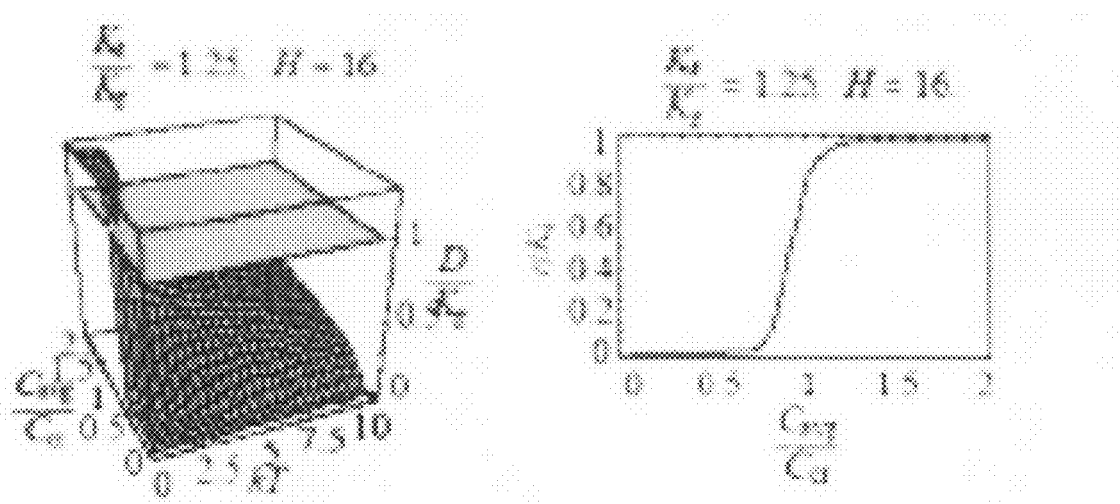
Fig. 4E
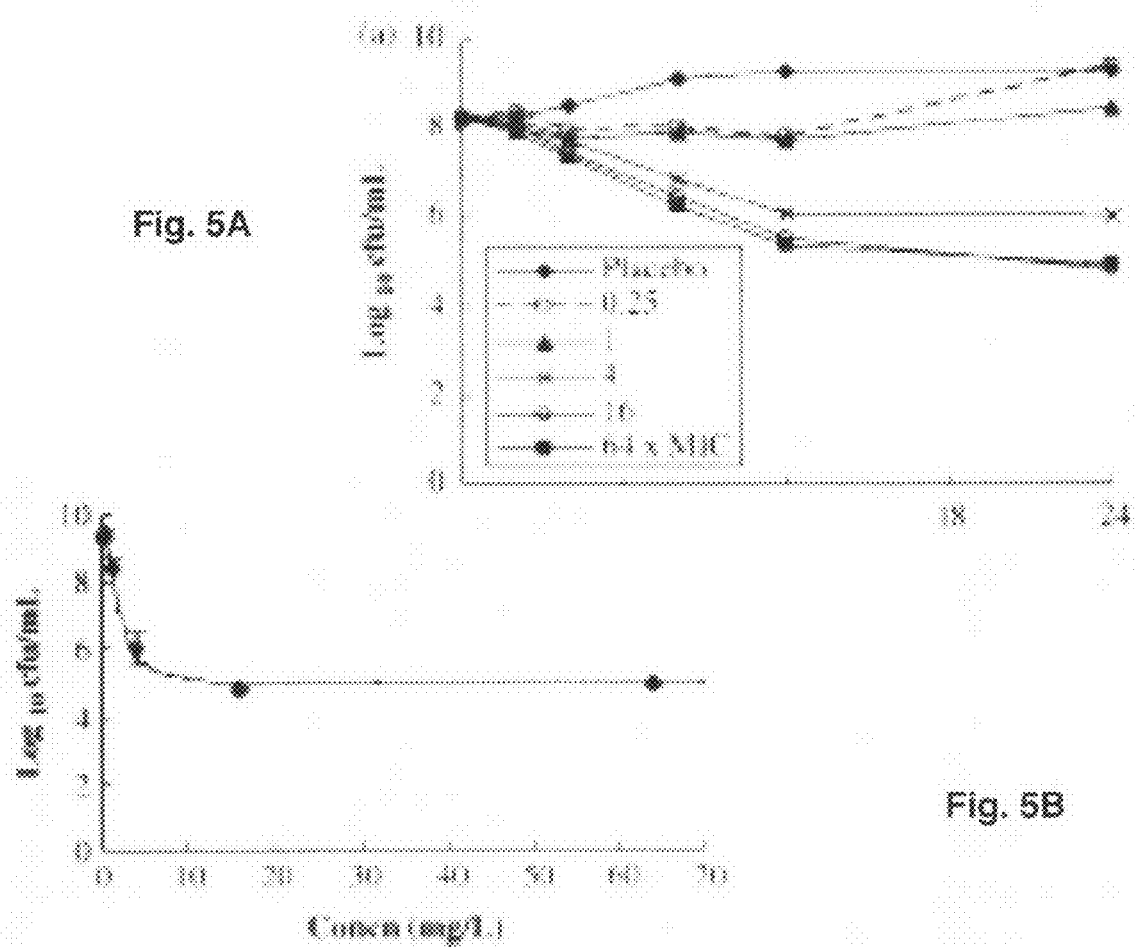
Fig. 5A
Fig. 5B

Experimental                                    Simulated

Experimental          Simulated

Experimental                    Simulated

Gram stain 100x

Gram stain 100x

Gram stain 400x

Gram stain 400x

Gram stain 1000x

HIGH THROUGHPUT SCREENING FOR ANTIMICROBIAL DOSING REGIMENS

CROSS-REFERENCE TO RELATED APPLICATION

This U.S. national stage application is filed under 35 U.S.C. 363 and claims benefit of priority under 35 U.S.C. 365 of international application PCT/US2006/036458, filed Sep. 19, 2006, now abandoned, which claims benefit of priority under 35 U.S.C. 119(e) of provisional U.S. Ser. No. 60/718,463, filed Sep. 19, 2005.

BACKGROUND OF THE INVENTION

1. Field of the Invention

The present invention relates generally to the fields of microbial pathology and acquired resistance of pathogens and mathematical modeling. More specifically, the present invention provides a computer-implemented method to predict acquisition of resistance within a microbial population to an antimicrobial agent and a screening tool to predict efficacy of potential antimicrobial agents in preventing acquisition of resistance within microbial populations.

2. Description of the Related Art

Resistance to antimicrobial agents is a serious problem that renders the rapid development of new agents an urgent priority. The alarming spread of antimicrobial resistance is threatening the therapeutic armamentarium (1-11). It has been estimated that nearly 2 million people in the U.S. acquire bacterial infections while in the hospital and about 90,000 of them die every year. The total cost of antimicrobial resistance to U.S. society is nearly $5 billion annually. It is likely that effective treatment may not be available for many common infections in the not too distant future and the risk of going back to the pre-antibiotic era in the event of an outbreak is present (4). Broad-spectrum antimicrobial resistance in HIV, tuberculosis, Gram-negative bacteria, e.g., *Pseudomaonas aeruginosa, Acinetobacter baumannii*, etc., and agents implicated in bioterrorism, e.g., *Bacillus anthracis*, is especially worrisome and has world-wide implications. It is therefore imperative that new and effective antimicrobial agents are developed rapidly to keep up with our combat against infections caused by these pathogens.

As widely appreciated as the magnitude of this problem may be, the traditional approach to the development of antimicrobial agents is unlikely to meet this critical need. The traditional approach has focused on the identification of new metabolic targets and agents to interfere with essential pathways. Relatively little attention has been paid to the impact of the dosing regimen, i.e., dose and dosing frequency, of an active agent on the emergence of resistance.

In-vitro and in-vivo experimental data demonstrate that dosing regimen may play an important role in the development of resistance; sub-optimal dosing regimens represent a selective pressure that facilitates resistance development, whereas using optimal dosing regimens may suppress the emergence of resistance (2-3, 12). However, multiple modifiable factors, e.g., the total daily dose, dosing frequency, length of (intravenous) administration and duration of therapy, etc., are involved in rational design of dosing regimens. Each factor may have a significant impact on the killing activity and propensity to suppress resistance emergence, depending on the pharmacodynamic properties of the agents and clinically achievable concentrations associated with acceptable toxicity.

The numerous combinations of these variables involved in designing dosing regimens are prohibitory for comprehensive laboratory or clinical evaluation of all the different scenarios. In view of the labor-intensiveness of each investigation, several regimens are often empirically chosen to be studied. This approach is poorly guided and may lead to prematurely abandoning the development of good agent candidates. As a result, the potentials of new agents may not be thoroughly realized.

Pharmacodynamic modeling has been used as a decision support tool to facilitate rational dosage design. It emphasizes the fact that effective antimicrobial treatment is attributed to neither antimicrobial agent potency (exposure) nor pathogen susceptibility alone, but rather a complex interplay of both factors. In spite of that, conventional modeling methods may be overly simplistic, relying on surrogate pharmacodynamic indices, e.g., area under the concentration-time profile (AUC)/minimum inhibitory concentration (MIC), percentage of dosing interval during which concentration is above MIC (% T>MIC), etc., to characterize outcomes. Conventional modeling methods typically take a snapshot of microbial burden at the end of an observation period and curve-fit the observations as a function of the surrogate index without making use of information at intermediate stages of the observation period (6-9, 13-16). Not surprisingly, these modeling approaches have restricted predictive ability and their limitations have been reviewed previously (17). On the other hand, modeling methods that make use of all available information on microbial burden during an observation period offer distinct advantages, in terms of being capable of accounting for the selective pressure that an antimicrobial agent exerts on a microbial population and to make useful predictions of microbial response to antimicrobial agents (18).

The ability to predict microbial response to antimicrobial agents is of great importance in the efforts in combating antimicrobial resistance. If the most effective dosing regimen of an antimicrobial agent can be identified and used clinically, it is hoped that the emergence of antimicrobial resistance can be suppressed (or delayed). Mathematical modeling and computer simulation of microbial response to antimicrobial agents hold great promise in accelerating and improving the development of antimicrobial agents. They have the capability to perform comprehensive screening of a large number of agent candidates to guide highly targeted testing. Thus, only promising agents and dosing regimens with high probabilities of success need be investigated subsequently in (pre-) clinical studies.

Thus, there is a significant need in the art for improvements in the area of high throughput screening for antimicrobial dosing regimens to increase the efficiency and cost-effectiveness of drug development. Specifically, the prior art is deficient in systems and methods of computer-implemented mathematical modeling useful to predict microbial response to a large number of antimicrobial agent and to design dosing regimens therefrom. The present invention fulfills this long-standing need and desire in the art.

SUMMARY OF THE INVENTION

The present invention is directed to a method for determining a best-fit mathematical model of adaptation of a microbial population to a therapeutic agent over time. The method comprises exposing the microbial population to a series of fixed concentrations of therapeutic agent over time and estimating parameter values for determining rates of change of the bacterial population over time in the presence of the therapeutic agent. A mathematical model is selected based on a best-fit of a combination of all estimated parameters values and distributions thereof over time that fit all the observed rates of change of the microbial population in a single step. The present invention is directed to a related method further comprising simulating behavior of a microbial population exposed to fluctuating therapeutic agent concentrations over time by inputting at least the estimated parameter values as initial parameter values into the mathematical model.

The present invention also is directed to a method for computer simulation to predict a likelihood of a population of cells associated with a pathophysiological condition acquiring resistance to a therapeutic agent. The method comprises storing a mathematical model of growth response over a period of time of a cell population in contact with a therapeutic agent in a computer having at least a memory, a processor and an input/output system. Initial parameter values are inputted into the mathematical model for determining at least susceptibility of the cells to the therapeutic agent and growth of a cell population during contact therewith over the period of time. Output values are generated predicting cellular susceptibility and cellular growth at incremental points over the time period. At or near the end of the time period, a decrease in cellular susceptibility output values and an increase in cell population growth values in a cell population which initially demonstrated susceptibility to the therapeutic agent with likelihood of acquisition of resistance of the cell population to the therapeutic agent. A decrease in cellular susceptibility output values and an increase in cell population growth values in a cell population which initially demonstrated susceptibility to the therapeutic agent at or near the end of the time period are correlated with a likelihood of acquisition of resistance of the cell population to the therapeutic agent.

The present invention is directed to a related method further comprising designing a dosing regimen that is pharmacologically effective against a cell population based on the output values over the time period of the mathematical model. The present invention is directed to another related method further comprising treating or preventing in a subject a pathophysiological condition caused by the cell population using the designed dosing regimen. The present invention is directed to yet another related method further comprising compiling a library of therapeutic agents and dosing regimens effective to suppress the emergence of acquired resistance in cell populations. The present invention is directed to still another related method further comprising screening a potential therapeutic agent for efficacy in suppressing resistance acquisition in one or more cell populations using the computer simulation.

The present invention is directed further to a method for suppressing emergence of acquired resistance of a cell population to an therapeutic agent useful for treating a pathophysiological condition associated therewith in a subject. The method comprises administering to the subject a pharmacologically effective amount of an therapeutic compound on a dosing regimen determined via the computer simulation of growth response over a period of time of a cell population in contact with the therapeutic agent described herein.

The present invention is directed further still to method for high-throughput screening for therapeutic agents effective to suppress emergence of acquired resistance thereto in a cell population associated with a pathophysiological condition. The method comprises inputting initial parameter values into a computer-implemented simulation utilizing a mathematical model comprising equations for calculating over a specified time period a rate of change of concentration of the therapeutic agent in the cell population, a rate of change of cellular susceptibility to the therapeutic agent and a rate of change of burden in a surviving cell population where the equations are operably linked to the initial parameter values described herein. During the computer simulation output values are generated predicting cellular susceptibility and cell growth at incremental points over the time period. An increase in cellular susceptibility output values and a decrease in cell population growth output values at or near the end of the time period is correlated with suppression of emergence of acquired resistance within the cell population to the therapeutic agent. The present invention is directed to a related method further comprising compiling a library of therapeutic agents and dosing regimens effective to suppress the emergence of acquired resistance in cell populations.

The present invention is directed further still to a computer-implemented system for high-throughput screening for therapeutic agents effective to suppress emergence of acquired resistance thereto in a cell population associated with a pathophysiological condition. The computer-implemented system comprises a memory storing a simulation of growth response over a period of time of a cell population in contact with the therapeutic agent and having processor executable instructions to perform the simulation, an input to the simulation of initial parameter values characterizing the cell population and the therapeutic agent, an output of simulation-generated values predictive of cell population growth in the presence of the therapeutic agent and cell population susceptibility to the therapeutic agent; and a module for correlating, at or near the end of the time period, a decrease in cellular susceptibility output values and an increase in cell population growth values in a cell population which initially demonstrated susceptibility to the therapeutic agent with a likelihood of acquisition of resistance of the cell population to the therapeutic agent. The present invention is directed to a related computer-implemented system comprising a module for designing a dosing regimen that is pharmacologically effective against a cell population based on the output values over the time period of the mathematical model. The present invention is directed to a further related computer-implemented system comprising a module for compiling a library of therapeutic agents and dosing regimens effective to suppress the emergence of acquired resistance in cell populations.

Other and further aspects, features and advantages of the present invention will be apparent from the following description of the presently preferred embodiments of the invention. These embodiments are given for the purpose of disclosure.

BRIEF DESCRIPTIONS OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 is an example of periodically fluctuating antimicrobial agent profile. Injection points can be seen every T hours. Decline of agent concentration is due to agent elimination.

FIGS. 2A-2B demonstrate eradication (FIG. 2A) or regrowth (FIG. 2B) of a microbial population in an environment of antimicrobial agent concentration as in FIG. 1.

FIGS. 4A-4E show a library of behaviors of $D/K_g$ as a function of kT and $C_{avg}/C_{cr}$.

FIGS. 5A-5B depict time-kill data of meropenem against *P. aeruginosa* (FIG. 5A) and the bacterial burden observed at 24 h modelled by an inhibitory sigmoid Emax model (FIG. 5B). Cm is the concentration of meropenem.

Figure 7A:
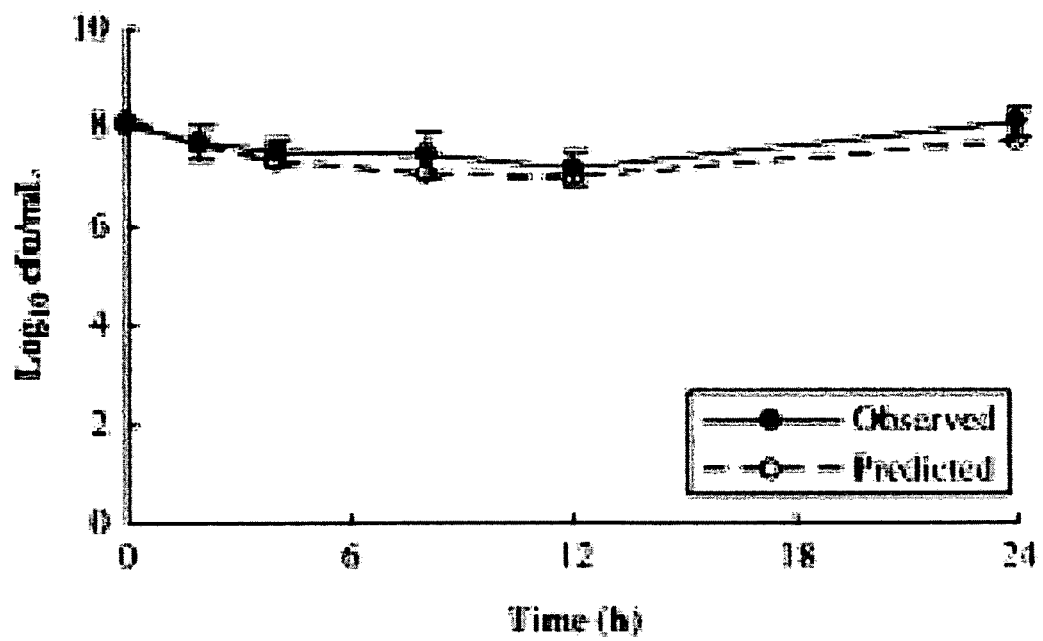
Figure 7B:
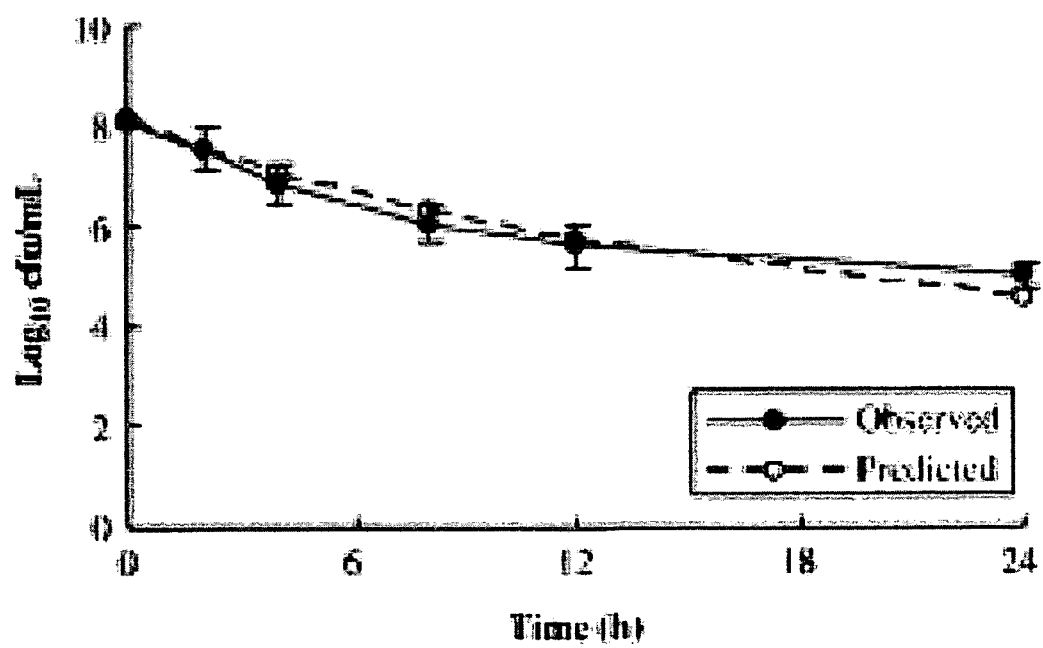

FIGS. 7A-7B are validations of the predictive performance of the model for meropenem at 2 MIC (FIG. 7A) and 32 MIC (FIG. 7B). Observations were based on duplicate time-kill studies performed on two separate days. The data represent the mean and SD of bacterial burden.

Figure 8A:
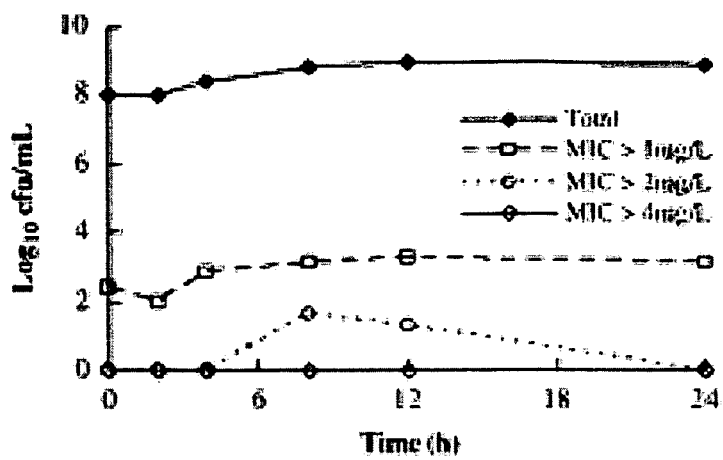
Figure 8B:
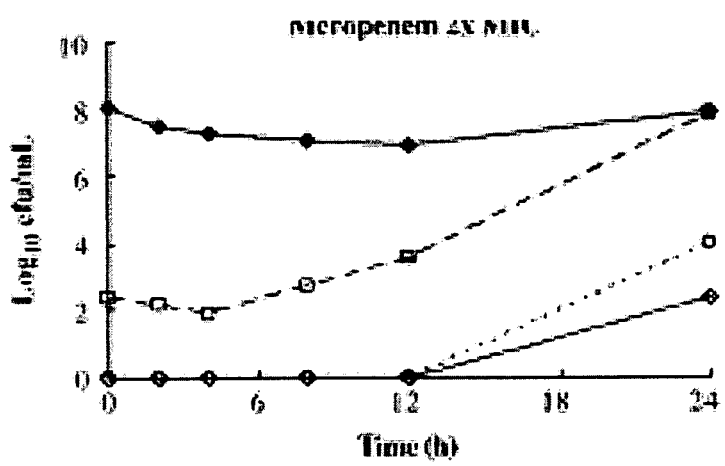
Figure 8C:
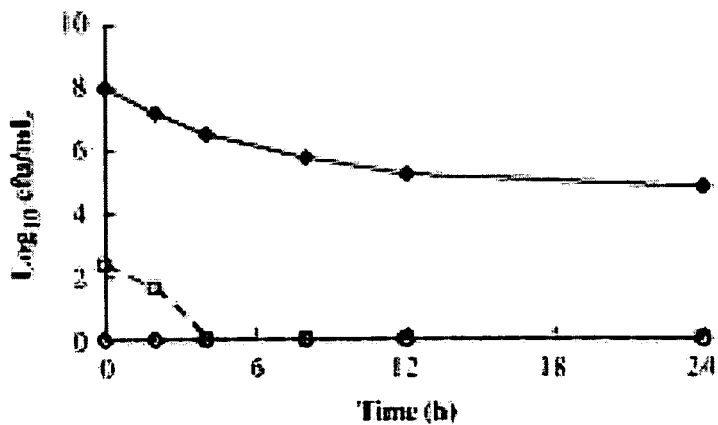

FIGS. 8A-8C are validation time-kill studies illustrating bacterial susceptibility distribution over time for placebo (FIG. 8A), meropenem at 2 MIC (FIG. 8B) and meropenem at 32 MIC (FIG. 8C). Bacterial burdens in samples were determined by quantitative cultures on drug-free MHA (total population), and MHA supplemented with meropenem at 1, 2 and 4 mg/L (subpopulations with reduced susceptibilities).

Figure 9A:
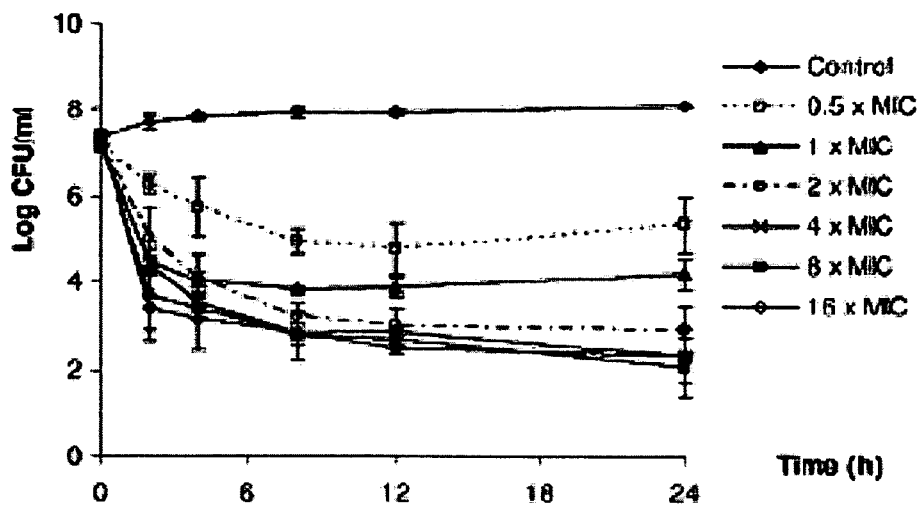
Figure 9B:
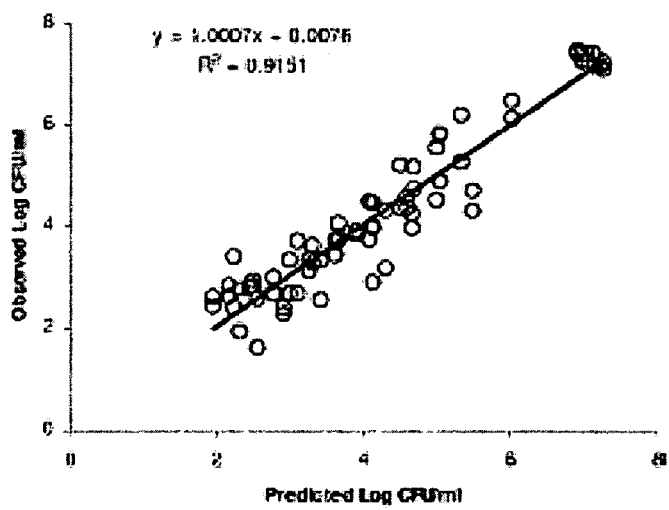
Figure 9C:
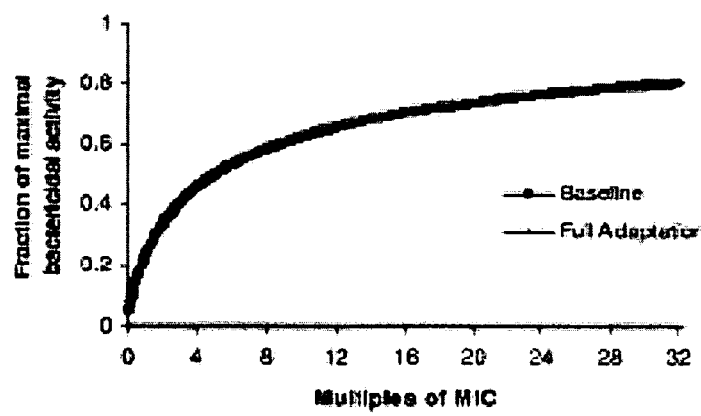

FIGS. 9A-9C depict time-kill studies of gentamicin (as multiples of MIC) against *S. aureus* ATCC 29213 (FIG. 9A), show correlations between observed and model-predicted bacterial burdens (FIG. 9B) and illustrates the relationship between gentamicin concentration, as a multiple of the MIC, and bactericidal activity, as a fraction of maximal killing, against *S. aureus* ATCC 29213 (FIG. 9C). Full adaptation refers to the entire bacterial population replaced by the most resistant clone (subpopulation) present at baseline. Data are presented as means±standard deviations based on duplicate experiments performed on different days.

Figure 10:
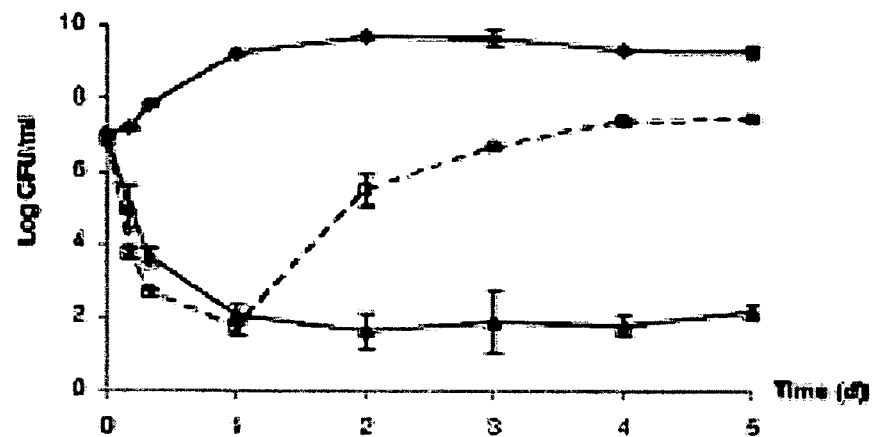

FIG. 10 illustrates the microbiologic response to different gentamicin exposures in hollow-fiber infection models for *S. aureus* ATCC 29213. Data are presented as means standard deviations.

Figure 11:
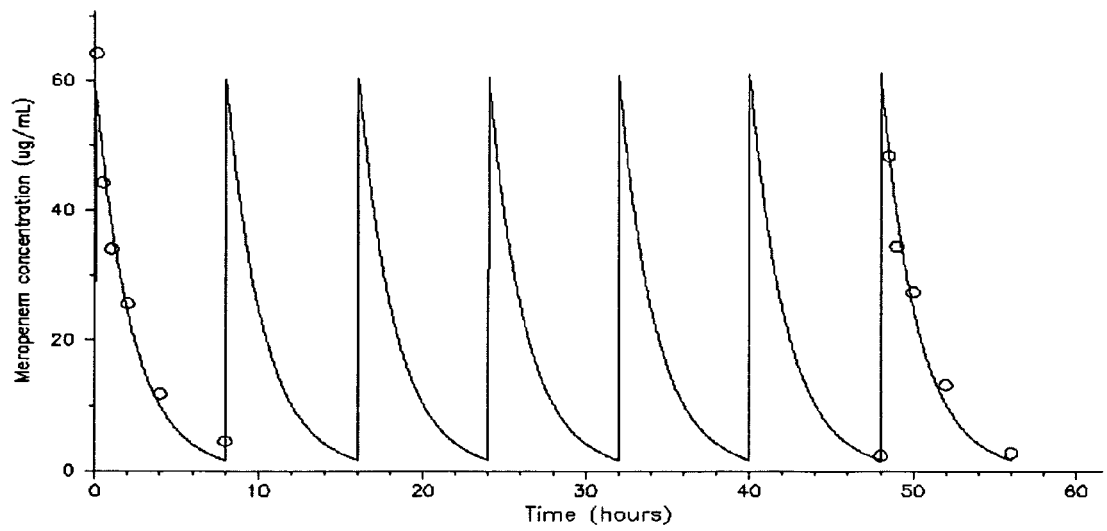
Figure 12A:
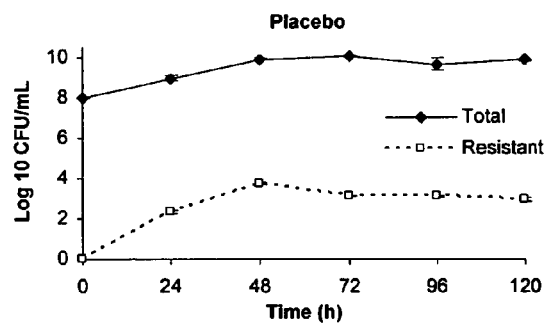
Figure 12B:
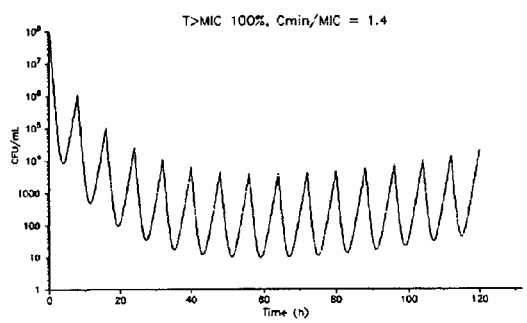
Figure 12B:
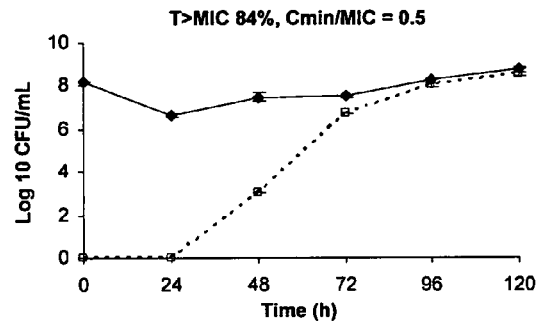
Figure 12C:
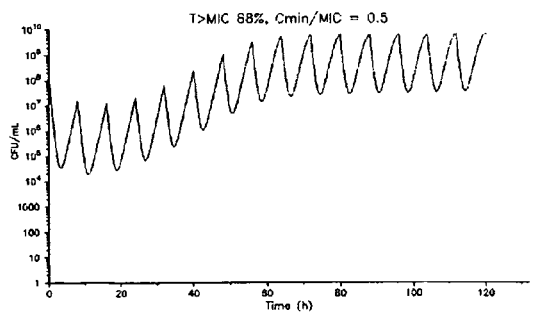
Figure 12C:
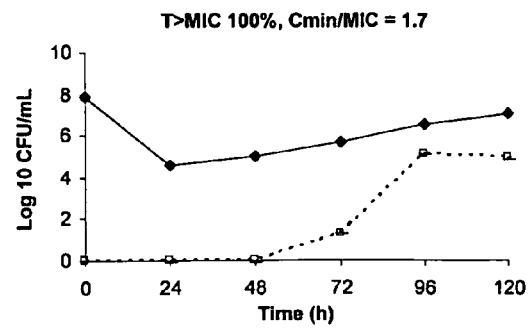
Figure 12D:
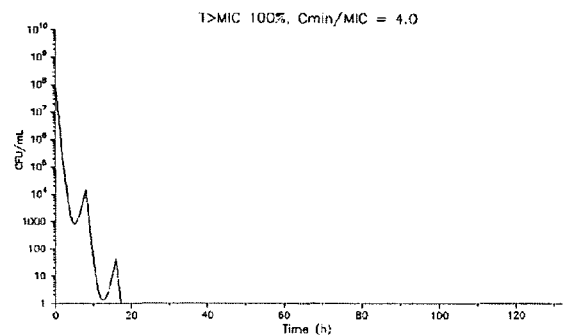
Figure 12E:
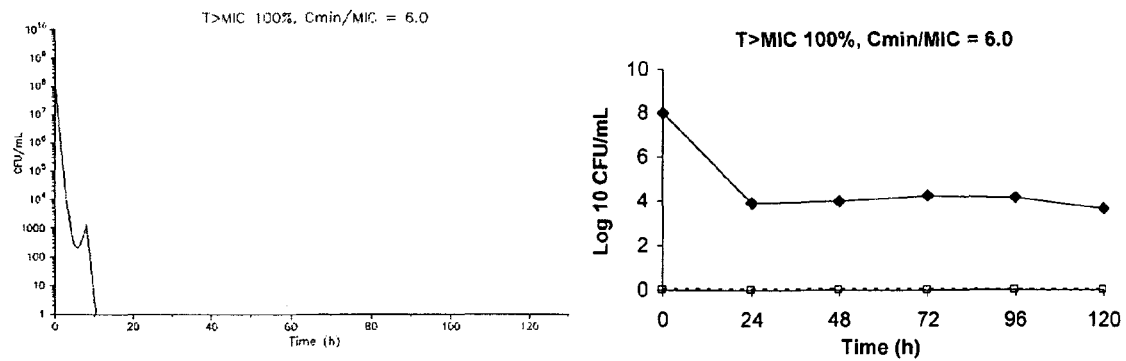

FIG. 11 illustrates a pharmacokinetic simulation in the hollow fiber infection model. $R^2=0.973$; $C_{max}=57.2$ mg/L; $C_{min}=1.7$ mg/L; T½=1.5 hours; T>MIC 100%; and $C_{min}$/MIC=1.7.

FIGS. 12A-12E compare computer-simulated and experimental bacterial response to various meropenem exposures. Doses were given every 8 hours for 5 days in all treatment regimens.

Figure 13:
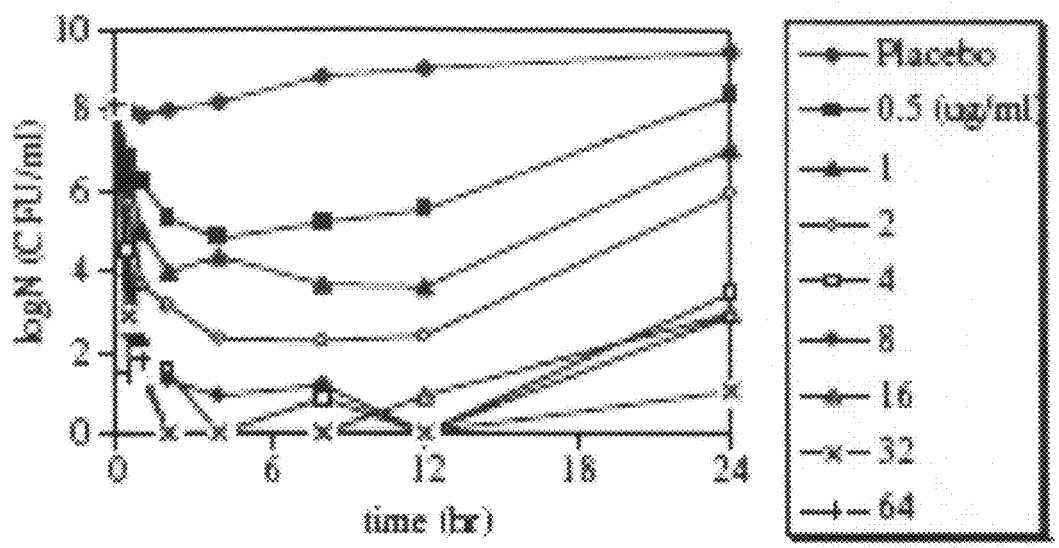

FIG. 13 shows time-kill studies of levofloxacin against *P. aeruginosa* ATCC 27853 (MIC=2 Ig/mL). For C=32× MIC=64 Ig/mL, there are no points beyond 1 h, since all bacteria appear to have been eradicated beyond that point in time.

Figure 14A:
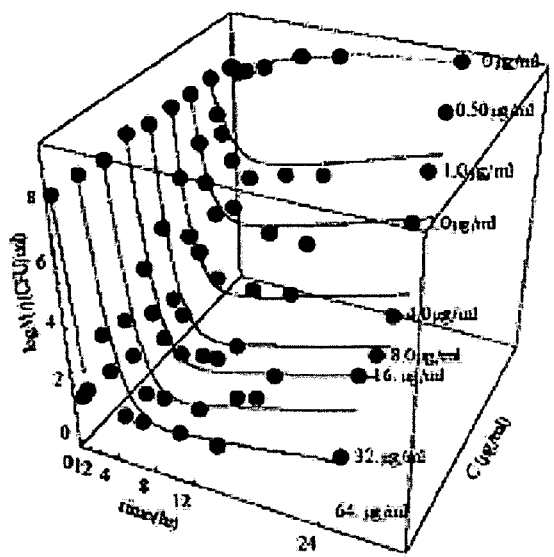
Figure 14B:
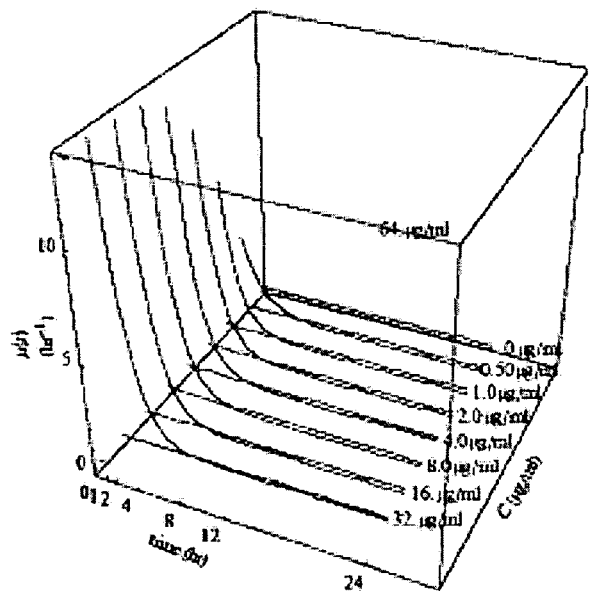
Figure 14C:
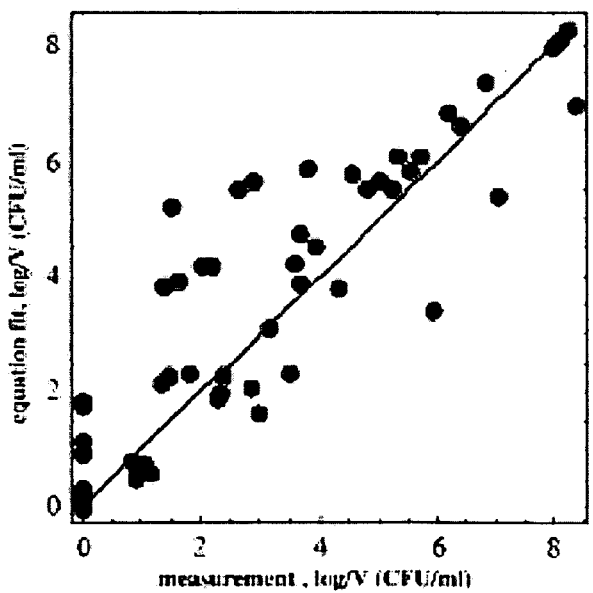

FIGS. 14A-14C depict the fit of the experimental data shown in FIG. 7 by the mathematical model of Eqs. (11) and (12) (FIGS. 14A-14B) and the correlation between experimental data and model fit ($R^2=0.83$) (FIG. 14C).

Figure 15:
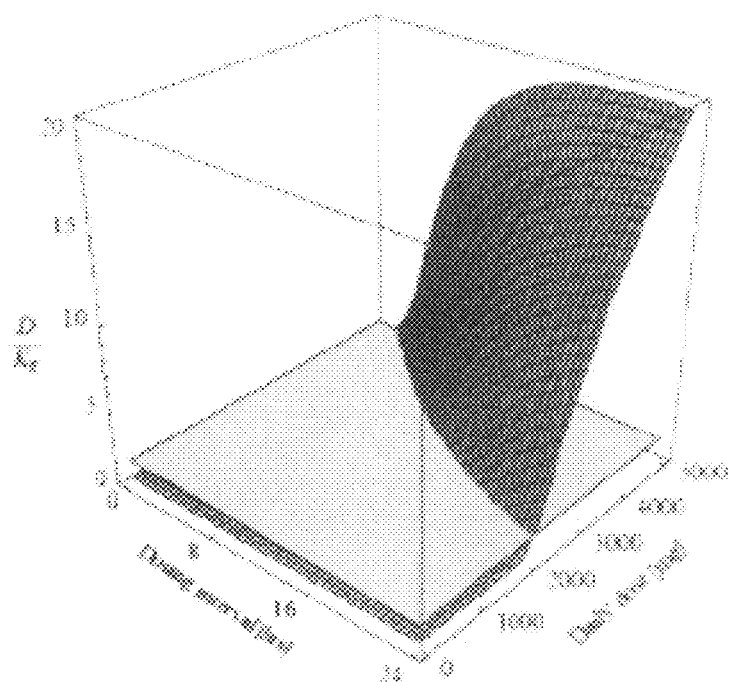

FIG. 15 shows a model prediction of bactericidal effect of levofloxacin for bacterial population of *P. aeruginosa*, corresponding to the time-kill data of FIG. 13. Figure parallels FIGS. 4A-4E for Cavg=Daily dose (mg)/24(h)9.24(l/H)×0.7 (where the 0.7 term is due to protein binding of 30%) and t½=6 h. Dosing regimens (combinations of daily dose and dosing interval) associated with resistance suppression correspond to $D/Kg \Rightarrow 1$, Eq (18).

Figure 16A:
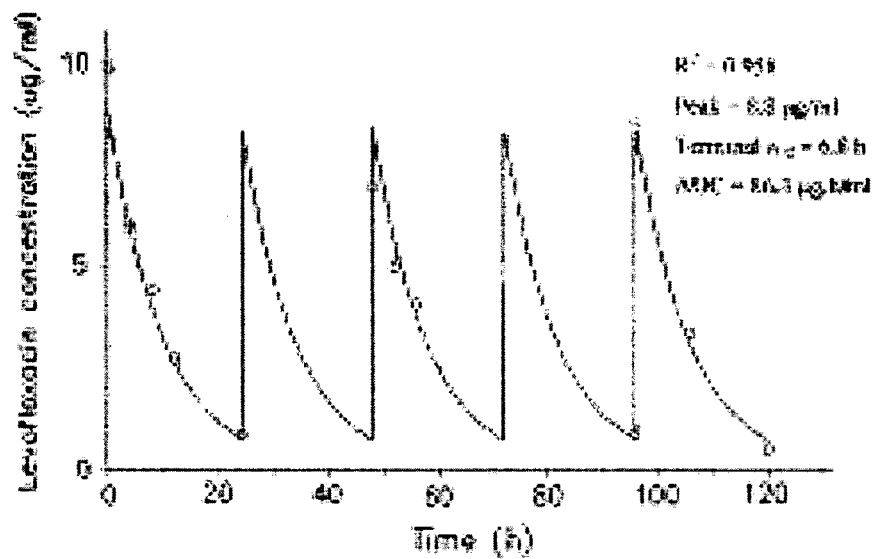
Figure 16B:
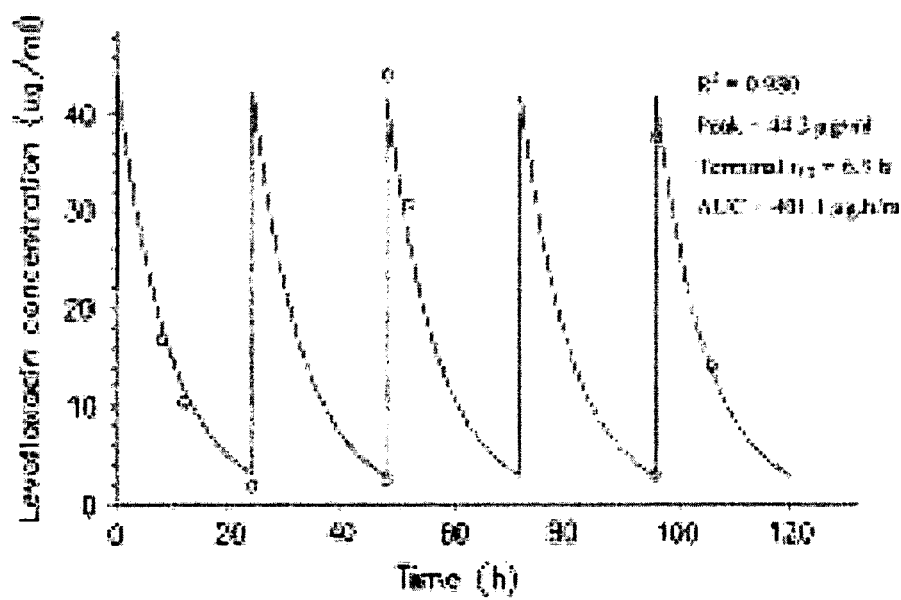

FIGS. 16A-16B depict simulated levofloxacin pharmacokinetic profiles; observed for daily dose of 750 mg (FIG. 16A), 3000 mg (FIG. 16B) given every 24 h.

Figure 17A:
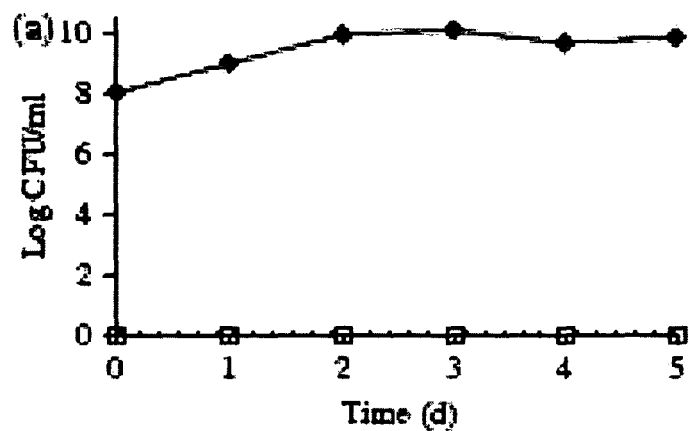
Figure 17B:
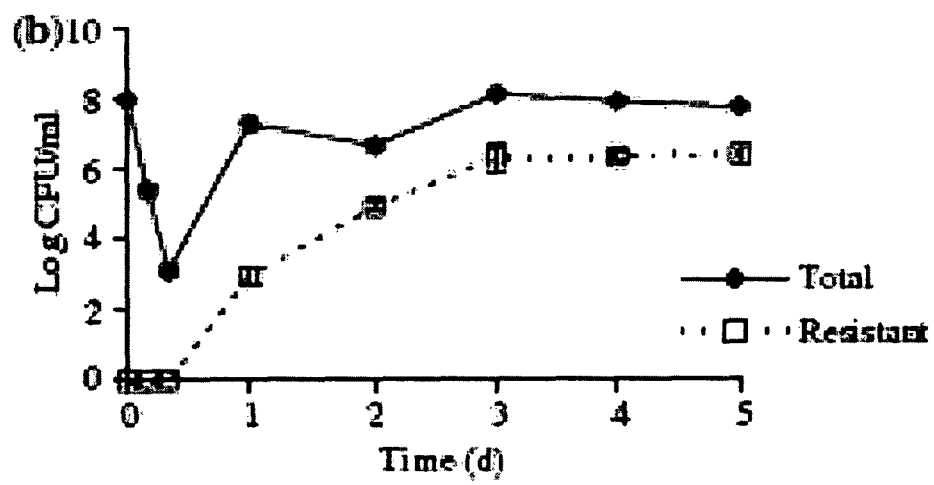
Figure 17C:
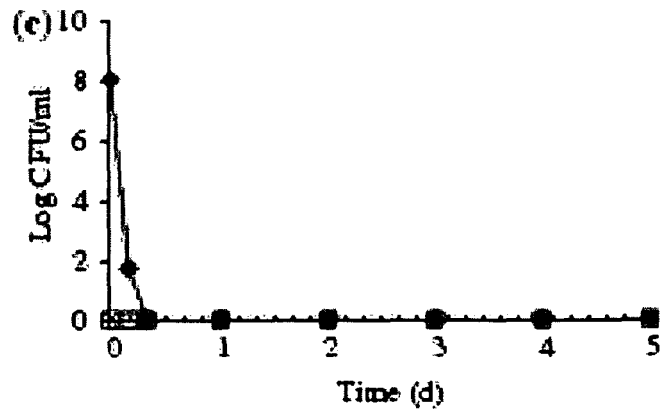

FIGS. 17A-17C illustrate the prospective validation of the mathematical model in the hollow-fiber infection model for placebo (FIG. 17A), levofloxacin 750 mg (FIG. 17B), levofloxacin 3000 mg (FIG. 17C) given every 24 h. Data presented as mean and standard deviation of duplicate samples.

Figure 18A:
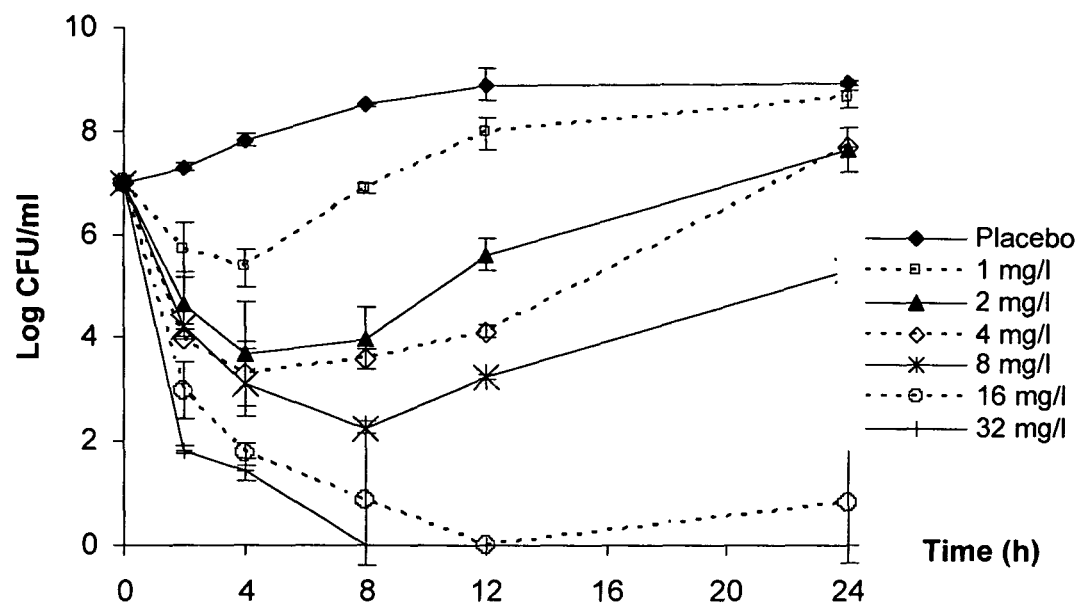
Figure 18B:
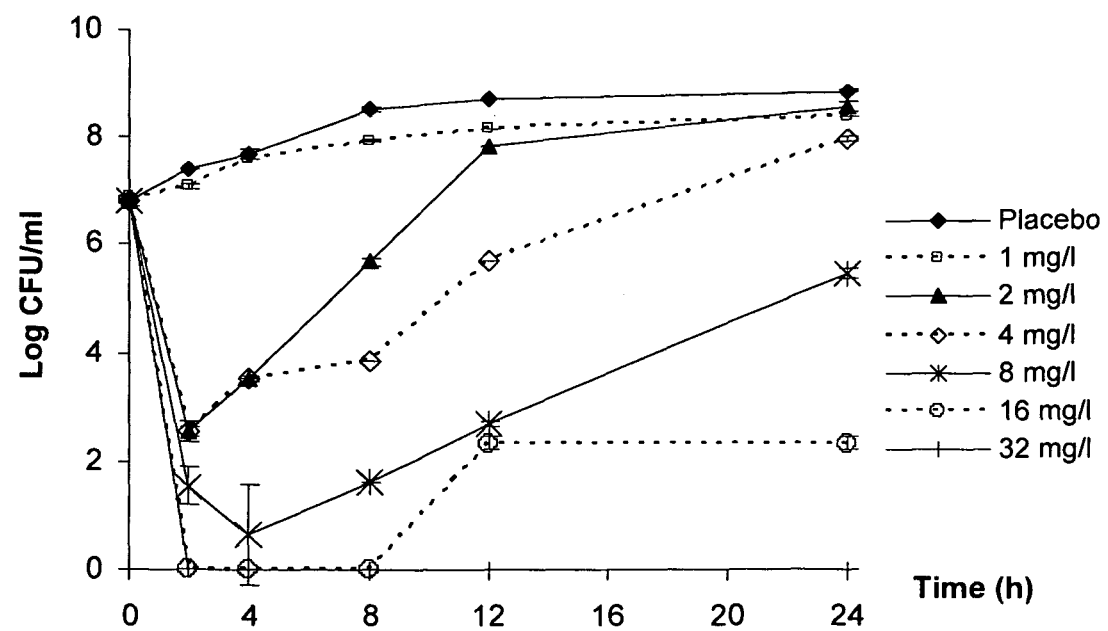

FIGS. 18A-18B depict time kill studies of gentamicin against *P. aeruginosa* ATCC 27853 (FIG. 18A) and amikacin against *A. baumannii* ATCC BAA 747 (FIG. 18B). Data shown as mean±standard deviation. Complete bacterial eradication was observed with amikacin concentrations>16 mg/l after 2 hours of drug exposure.

Figure 19A:
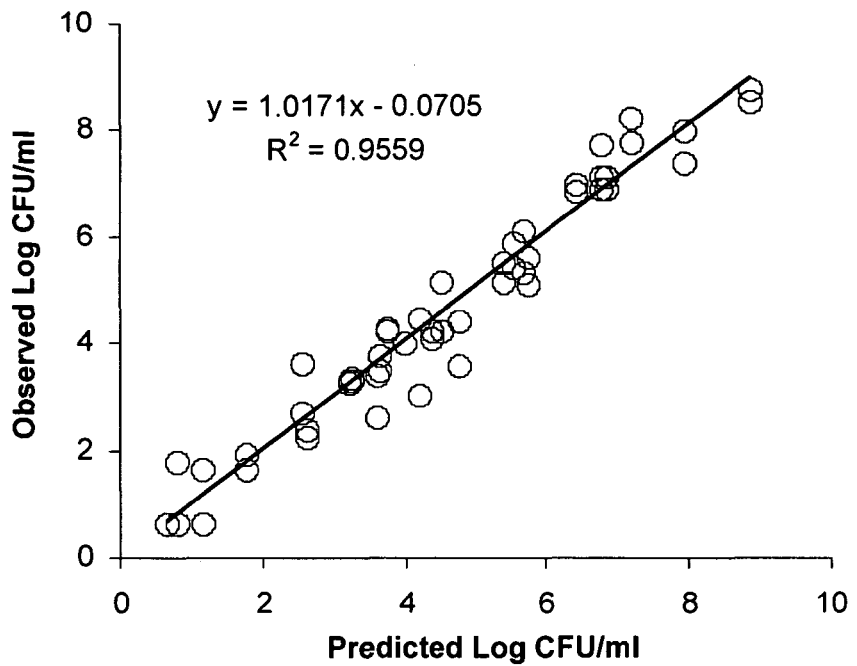
Figure 19B:
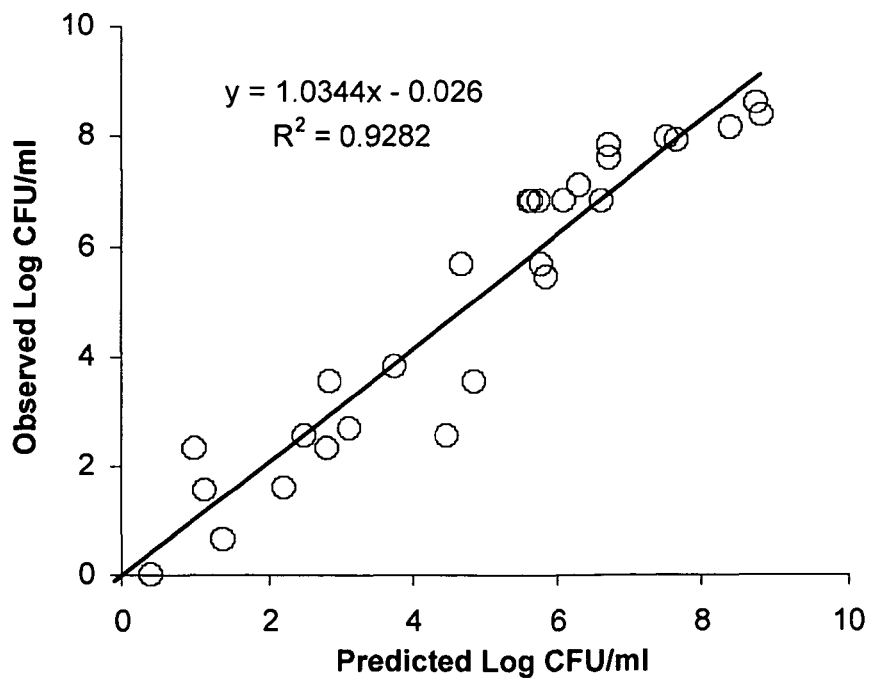
Figure 20A:
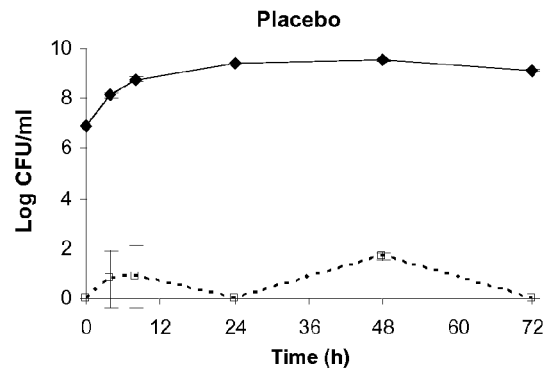
Figure 20B:
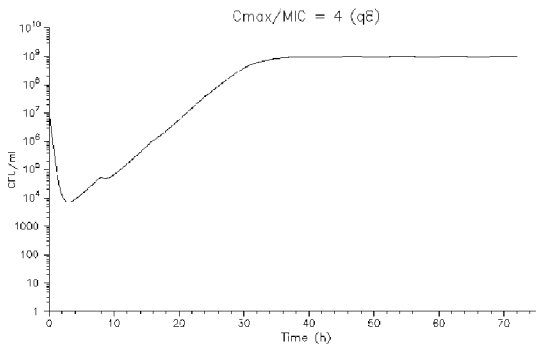
Figure 20B:
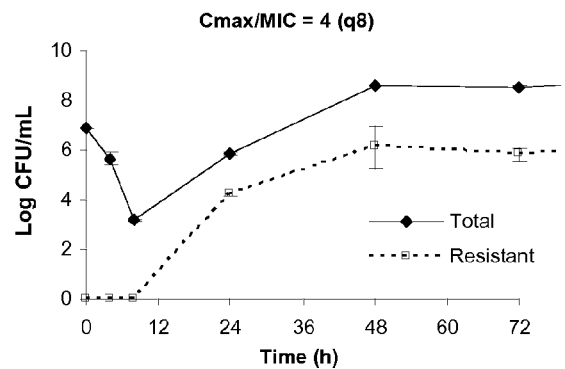
Figure 20C:
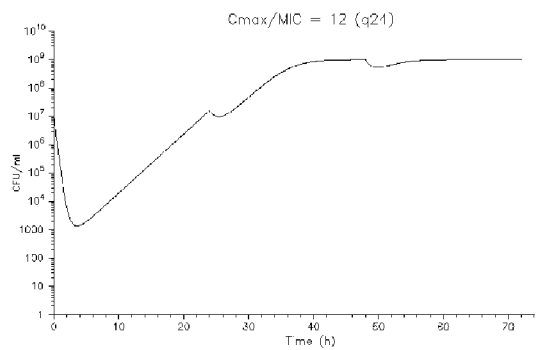
Figure 20C:
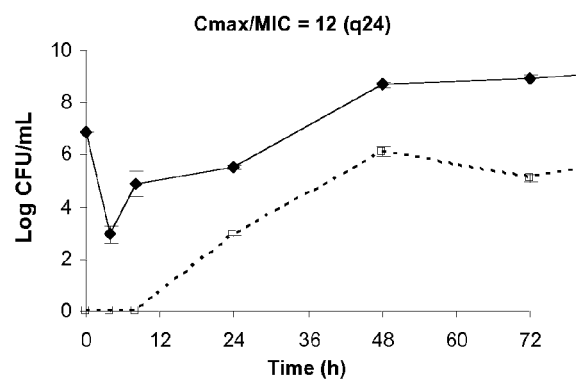
Figure 20D:
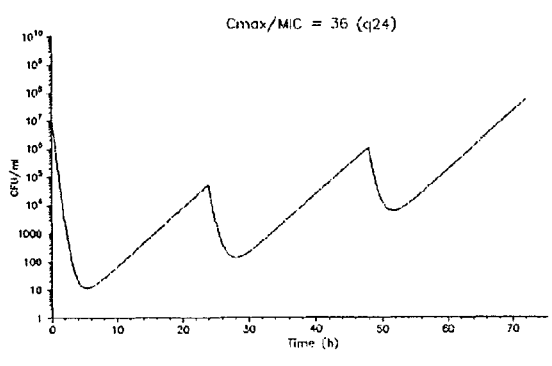
Figure 20D:
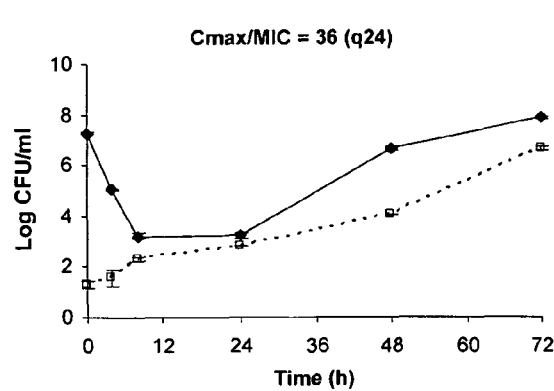
Figure 20E:
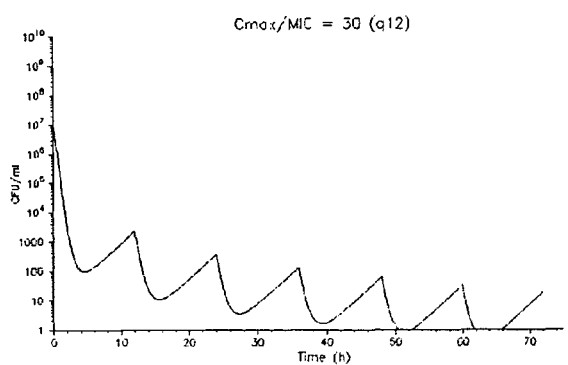
Figure 20E:
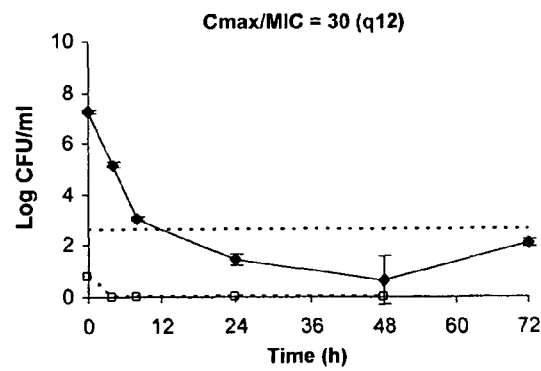

FIGS. 19A-19B demonstrates that the model fits to the experimental data. Gentamicin against *P. aeruginosa* ATCC 27853 (FIG. 19A) and amikacin against *A. baumannii* ATCC BAA 747 (FIG. 19B)

FIGS. 20A-20E are a comparison of computer-simulated and experimental bacterial response to various gentamicin exposures. Dosing frequency is in parentheses. Data shown as mean±standard deviation. The horizontal dotted line in Cmax/MIC=30, every 12 h) depicts the reliable lower limit of detection.

Figure 21:
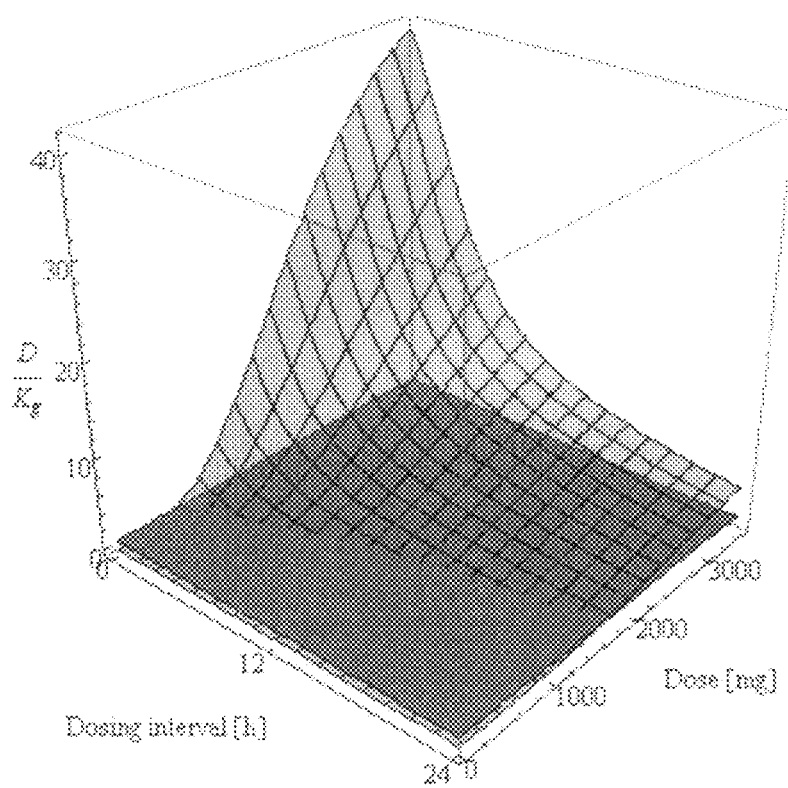

FIG. 21 illustrates the likelihood of bacterial resistance emergence to various dosing regimens of amikacin as predicted by a response surface analysis. Two intersecting planes are shown: a translucent mesh surface (representing different dosing regimens) and an opaque surface (where $D/K_g=1$). The 3-dimensional mesh surface is made up of a collection of data points; each datum point is characterized by a value on the x, y and z axes, corresponding to the dose (x), dosing interval (y) and $D/K_g$ (z). Cmax/MIC=Dose/(Volume of distribution*MIC)=Dose/(70*0.35*4).

Figure 22A:
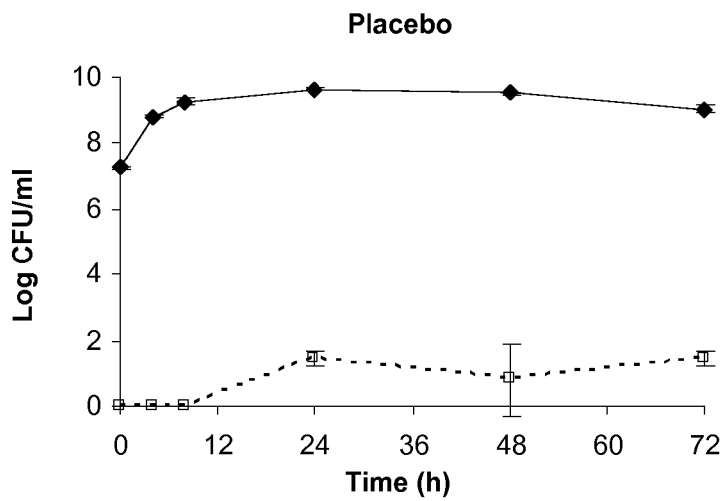
Figure 22B:
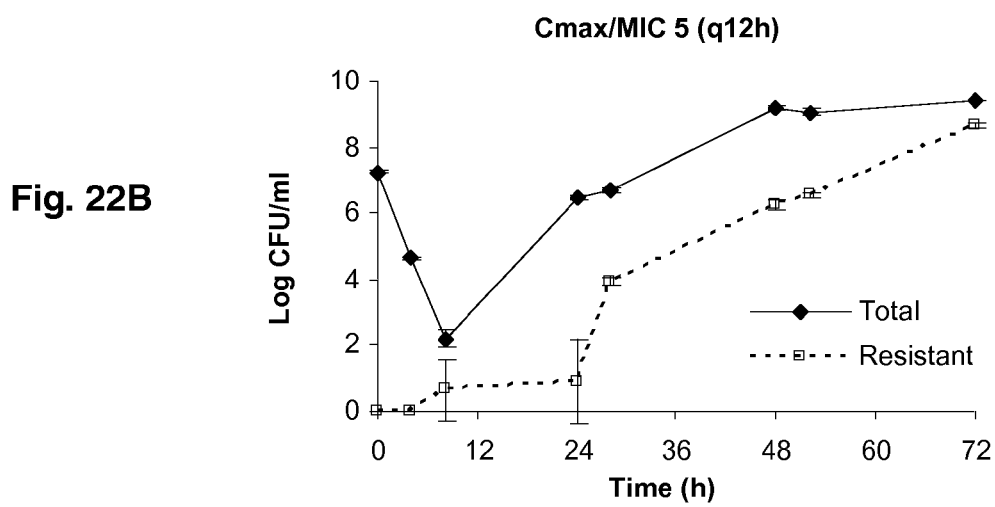
Figure 22C:
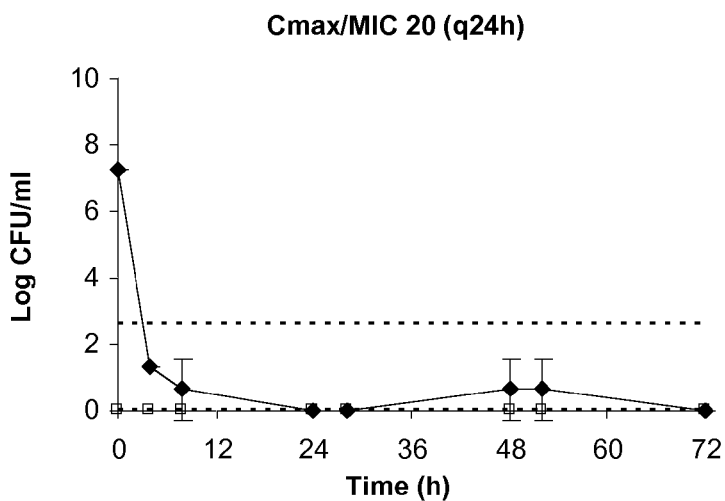

FIGS. 22A-22C show prospective validations of microbial response to various amikacin dosing regimens. Dosing frequency is in parentheses. Data shown as mean±standard deviation. The horizontal dotted line depicts the reliable lower limit of detection.

Figure 23:
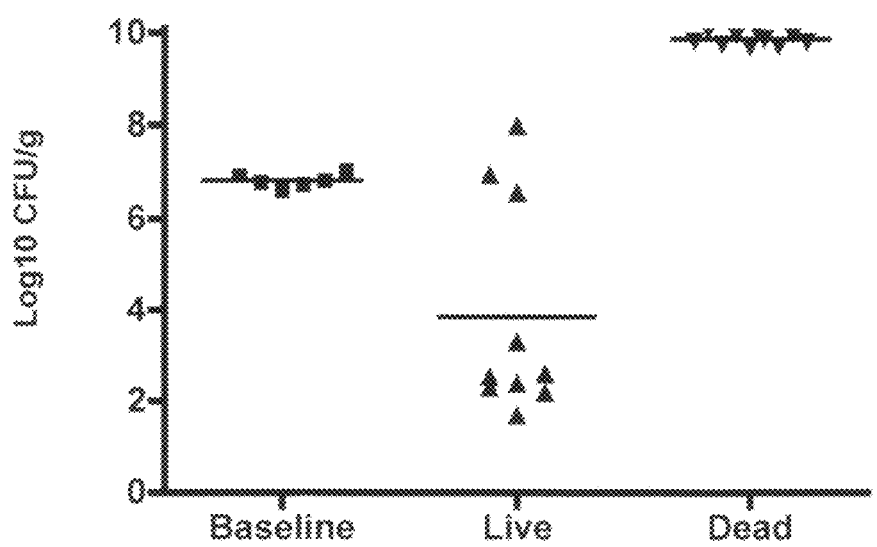

FIG. 23 shows the bacterial burden in lung tissues before treatment was given (baseline), at the end of experiment (live) and at the time of death (dead)

Figure 24A:
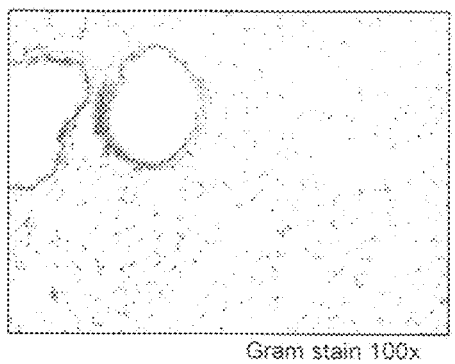
Figure 24C:
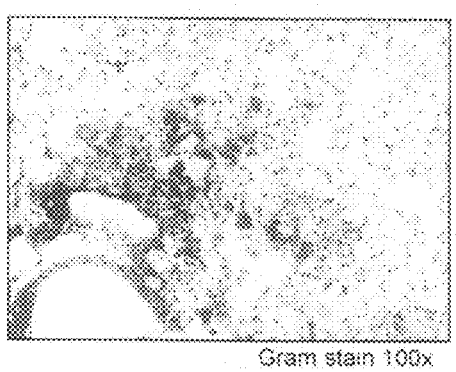
Figure 24B:
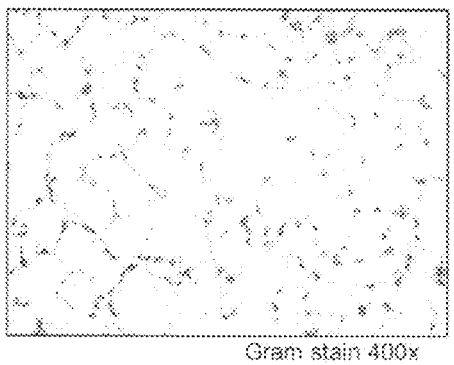
Figure 24D:
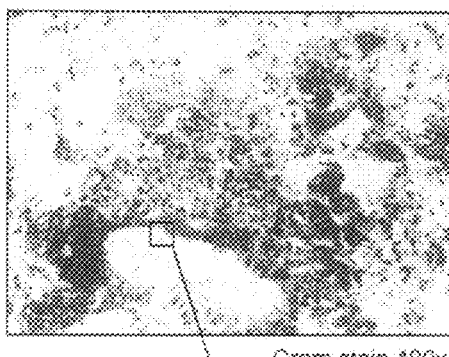
Figure 24E:
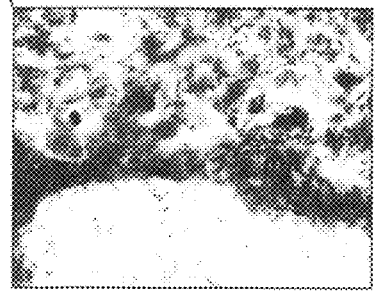

FIGS. 24A-24E depict the histopathologic examination of lung tissues. Baseline 100× (FIG. 24A), 400× (FIG. 24B); 24 hours after infection 100× (FIG. 24C); 400× (FIG. 24D); 1000× (FIG. 24E).

Figure 25:
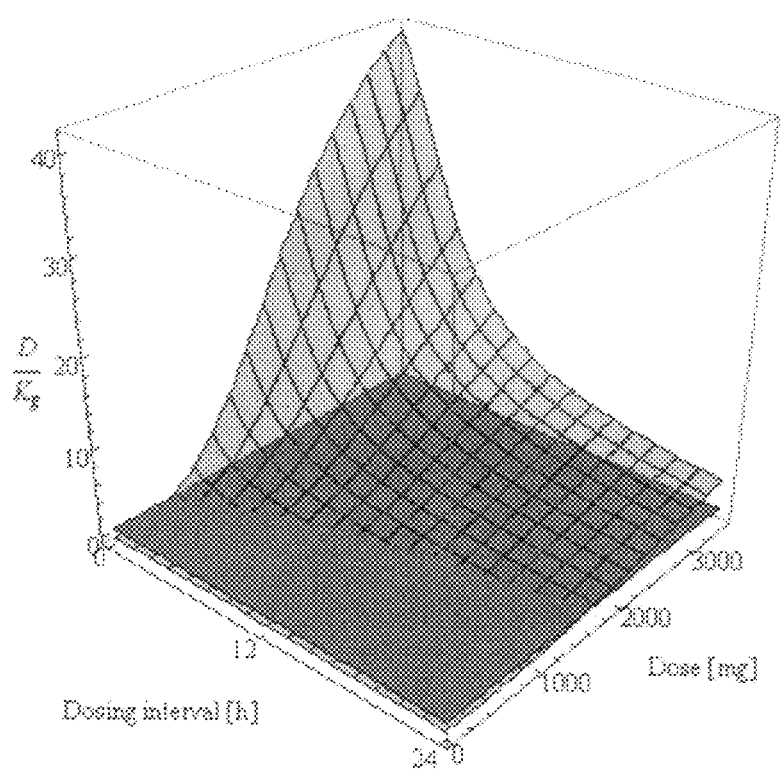

FIG. 25 shows the pharmacokinetics of meropenem in mice with transient nephrotoxicity. Data represent mean±standard error of the means.

Figure 26A:
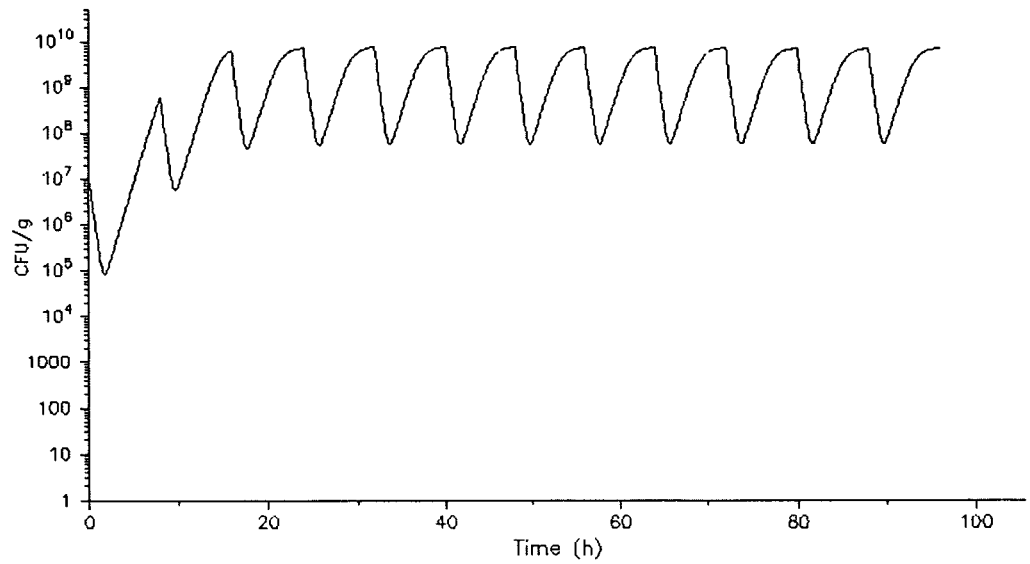
Figure 26B:
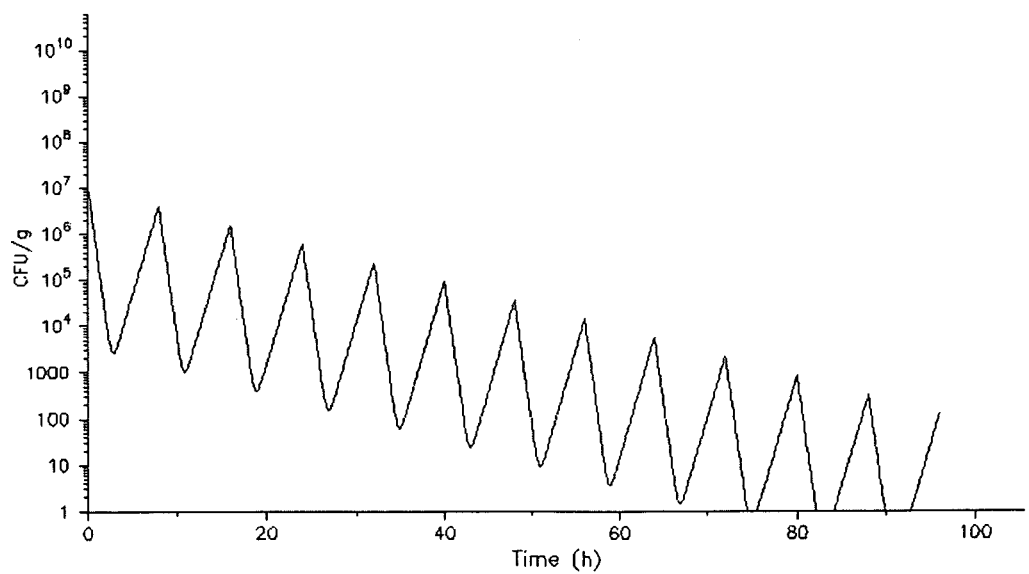

FIGS. 26A-26B are mathematical simulations of bacterial response to meropenem in a heterogeneous population (FIG. 26A) and a homogeneous population (FIG. 26B).

Figure 27:
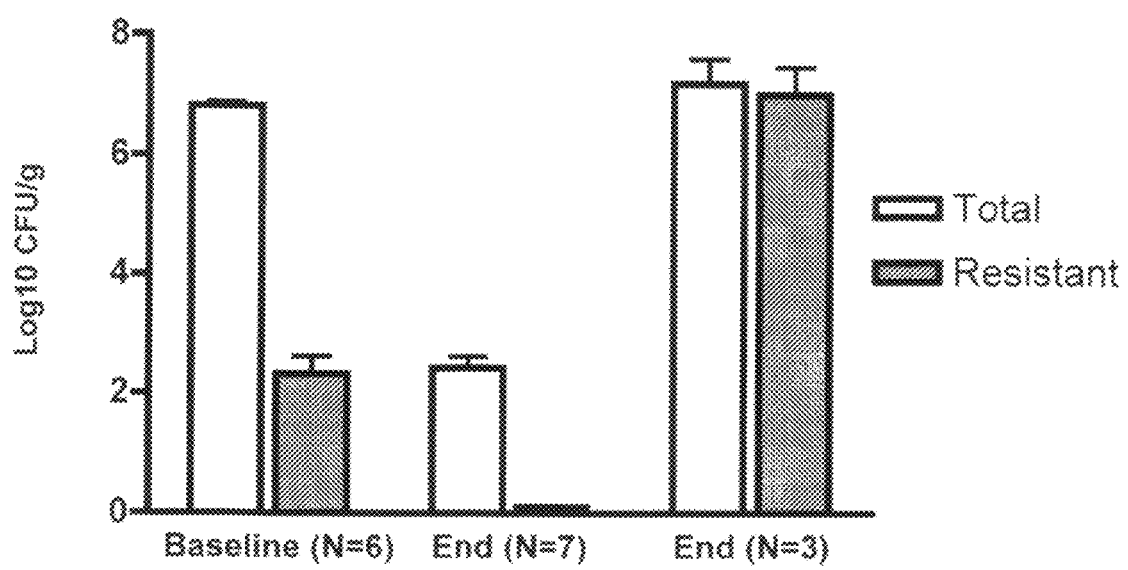

FIG. 27 demonstrates the microbial burden in live mice after exposure to a sub-optimal meropenem exposure. Data represent mean±standard error of the means. All 10 mice received meropenem treatment survived up to 96 hours, but resistance emergence was found in 3 mice.

DETAILED DESCRIPTION OF THE INVENTION

As used herein, the term "a" or "an" may mean one or more. As used herein in the claim(s), when used in conjunction with the word "comprising", the words "a" or "an" may mean one or more than one. As used herein "another" or "other" may mean at least a second or more of the same or different claim element of components thereof. Some embodiments of the invention may consist of or consist essentially of one or more elements, method steps, and/or methods of the invention.

As used herein, the term "or" in the claims refers to "and/or" unless explicitly indicated to refer to alternatives only or the alternatives are mutually exclusive, although the disclosure supports a definition that refers to only alternatives and "and/or."

As used herein, the term "contact" refers to any suitable method or means whereby an antimicrobial agent is brought into contact with a microbial population, i.e., one or more, including all, of the microorganisms comprising the population. In vitro or ex vivo this is achieved by exposing the microbial population or microorganisms comprising the same to the antimicrobial agent in a suitable medium. For in vivo applications, any known method of administration is suitable as described herein.

As used herein, the term "subject" refers to a mammal, preferably a human that is the recipient of a therapeutic or pharmacologically effective or prophylatic treatment for a pathophysiological condition associated with a microbial population.

As used herein, the term "therapeutic agent" refers to any known or potential antimicrobial compounds or any known or potential chemotherapeutic compounds effective to suppress acquisition of resistance in a microbial or tumor cell population.

As used herein, the term "cell population" refers to both a microbial population or a population of cancer cells comprising, for example, a tumor.

The following abbreviations are used herein: MEM: meropenem; PIP: piperacillin; CAZ: ceftazidime; IPM: imipenem; LVX: levofloxacin; TOB: tobramycin; ND: not determined; OprD−: porin deletion; Mex+: MexAB-OprM efflux pump over-expression.

In one embodiment of the present invention there is provided a method for determining a best-fit mathematical model of adaptation of a microbial population to a therapeutic agent over time, comprising exposing the microbial population to a series of fixed concentrations of therapeutic agent over time; estimating parameter values for determining rates of change of the bacterial population over time in the presence of the therapeutic agent; and selecting a mathematical model based on a best-fit of a combination of all estimated parameters values and distributions thereof over time that fit all the observed rates of change of the microbial population in a single step.

Further to this embodiment the method comprises simulating behavior of a microbial population exposed to fluctuating therapeutic agent concentrations over time by inputting at least the estimated parameter values as initial parameter values into the mathematical model. In this further embodiment the initial input parameters further may comprise infusion rate of the therapeutic agent, volume of distribution, clearance of the therapeutic agent, concentration to achieve 50% of maximal kill rate of a cell population. Also, the mathematical model may calculate over a specified time period a rate of change of concentration of the therapeutic agent in the cell population, a rate of change of cellular susceptibility to the therapeutic agent and a rate of change of cell burden in a surviving cell population.

In both embodiments the estimated parameters may comprise a growth rate constant for the microbial population, concentration of the bacterial population at time t, maximum population size, concentration of the therapeutic agent at time t, a maximal kill rate constant for the microbial population by the therapeutic agent, sigmoidicity constant for the microbial population, an adaptation function, maximal adaptation, and a rate of adaptation factor. Also, the rate of change of the microbial population over time may be equal to an intrinsic growth rate minus a kill rate by the therapeutic agent.

In another embodiment of the present invention there is provided a method for computer simulation to predict a likelihood of a population of cells associated with a pathophysiological condition acquiring resistance to a therapeutic agent, comprising a) storing a mathematical model of growth response over a period of time of a cell population in contact with a therapeutic agent in a computer having at least a memory, a processor and an input/output system; b) inputting initial parameter values into the mathematical model for determining at least susceptibility of the cells to the therapeutic agent and growth of a cell population during contact therewith over the period of time; c) generating output values predicting cellular susceptibility and cellular growth at incremental points over the time period; and d) correlating, at or near the end of the time period, a decrease in cellular susceptibility output values and an increase in cell population growth values in a cell population which initially demonstrated susceptibility to the therapeutic agent with likelihood of acquisition of resistance of the cell population to the therapeutic agent.

In a further embodiment the method comprises designing a dosing regimen that is pharmacologically effective against the cell population based on the output values over the time period of the mathematical model. Further still the method comprises treating or preventing in a subject a pathophysiological condition caused by the cell population using the designed dosing regimen. An example of a pathophysiological condition is a nosocomial infection or a cancer.

In another further embodiment the method comprises compiling a library of therapeutic agents and dosing regimens effective to suppress the emergence of acquired resistance in cell populations. In yet another further embodiment the method comprises screening a potential therapeutic agent for efficacy in suppressing resistance acquisition in one or more cell populations using the computer-implemented simulation.

In all embodiments the initial parameters input into the mathematical model in step b) may comprise time, infusion rate of the therapeutic agent, volume of distribution, clearance of the therapeutic agent, concentration to achieve 50% of maximal kill rate of a cell population, and maximum size of a cell population and constants for maximum adaptation and adaptation rate of a cell population and growth rate, maximum kill rate and sigmoidicity of a cell population. Also, the step of generating output values in step c) may comprise calculating from equations into which the initial parameter values are inputted over a specified time period a rate of change of concentration of the therapeutic agent in the cell population, a rate of change of cellular susceptibility to the therapeutic agent and a rate of change of burden in a surviving cell population.

Also in all embodiments the cell population may be a microbial population of Gram negative bacteria, Gram positive bacteria, yeast, mold, mycobacteria, virus, or infectious agents used in bioterroism. Representative examples of Gram negative bacteria are *Escherichia coli, Klebsiella pneumoniae, Pseudomaonas aeruginosa* and *Acinetobacter baumannii*. Representative examples of Gram positive bacteria are *Streptococcus pneumoniae* and *Staphylococcus aureus*. A representative example of a virus is HIV or avian influenza. A representative example of an infectious agent used in bioterrorism is *Bacillus anthracis*.

In yet another embodiment of the present invention there is provided a method for suppressing emergence of acquired resistance of a cell population to a therapeutic agent useful for treating a pathophysiological condition associated therewith in a subject, comprising administering to the subject a pharmacologically effective amount of a therapeutic agent on a dosing regimen determined via a computer simulation of growth response over a period of time of a cell population in contact with the therapeutic agent.

In this embodiment the computer simulation is stored in a computer memory and is executed by a processor where the simulation is adapted to utilize at least an input/output system to input initial parameter values into a mathematical model to determine at least cell susceptibility to the therapeutic agent and growth of a cell population during contact therewith over the period of time and to generate output values predicting cellular susceptibility and cell growth at incremental points over the time period. The mathematical model may comprise, as operably linked components equations for calculating over a specified time period a rate of change of concentration of the therapeutic agent in the cell population, a rate of change of cellular susceptibility to the therapeutic agent and a rate of change of cell burden in a surviving cell population and initial parameter values for the equations corresponding to time, infusion rate of the therapeutic agent, volume of distribution, clearance of the therapeutic, concentration to achieve 50% of maximal kill rate of a cell population, and maximum size of a cell population and constants for maximum adaptation and adaptation rate of a cell population and growth rate, maximum kill rate and sigmoidicity of a cell population.

Also in this embodiment the dosing regimen may be determined at least from the output values over the time period of the mathematical model. The pathophysiological conditions and cell populations are as described supra.

In yet another embodiment of the present invention there is provided method for high-throughput screening for therapeutic agents effective to suppress emergence of acquired resistance thereto in a cell population associated with a pathophysiological condition, comprising inputting initial parameter values into a computer-implemented simulation utilizing a mathematical model comprising equations for calculating over a specified time period a rate of change of concentration of the therapeutic agent in the cell population, a rate of change of cellular susceptibility to the therapeutic agent and a rate of change of cell burden in a surviving cell population, said equations operably linked to the initial parameter values; generating output values during the computer simulation predicting cellular susceptibility and cell growth at incremental points over the time period; and correlating, at or near the end of the time period, an increase in cellular susceptibility output values and a decrease in cell population growth values with suppression of emergence of acquired resistance within the cell population to the therapeutic agent.

Further to this embodiment the method comprises compiling a library of therapeutic agents and dosing regimens effective to suppress the emergence of acquired resistance in cell populations. In both embodiments the cell population and pathophysiological condition may be as described supra. Also, in both embodiments the initial parameter values may correspond to time, infusion rate of the therapeutic, volume of distribution, clearance of the therapeutic, concentration to achieve 50% of maximal kill rate of a cell population, and maximum size of a cell population and constants for maximum adaptation and adaptation rate of a cell population and growth rate, maximum kill rate and sigmoidicity of a cell population.

In yet another embodiment of the present invention there is provided a computer-implemented system for high-throughput screening for therapeutic agents effective to suppress emergence of acquired resistance thereto in a cell population associated with a pathophysiological condition, comprising a memory storing a simulation of growth response over a period of time of a cell population in contact with the therapeutic agent and having processor executable instructions to perform the simulation; an input to the simulation of initial parameter values characterizing the cell population and the therapeutic agent; an output of simulation-generated values predictive of cell population growth in the presence of the therapeutic agent and cell population susceptibility to the therapeutic agent; and a module for correlating, at or near the end of the time period, a decrease in cellular susceptibility output values and an increase in cell population growth values in a cell population which initially demonstrated susceptibility to the therapeutic agent with a likelihood of acquisition of resistance of the cell population to the therapeutic agent.

Further to this embodiment the computer-implemented system may comprise a module for designing a dosing regimen that is pharmacologically effective against a cell population based on the output values over the time period of the mathematical model. In another further embodiment the computer-implemented system may a module for compiling a library of therapeutic agents and dosing regimens effective to suppress the emergence of acquired resistance in cell populations.

In all embodiments the simulation may utilize a mathematical model comprising, as operably linked components, equations calculating over a specified time period a rate of change of concentration of the therapeutic agent in the cell population, a rate of change of cellular susceptibility to the therapeutic agent and a rate of change of burden in a surviving cell population, said equations generating the output values from the inputted initial parameter values. Also, the pathophysiological condition may be a nosocomial infection or a cancer.

Provided herein are mathematical models and computer-implemented methods and simulation approaches useful as a high throughput screening tool to facilitate rational dosing design in antimicrobial agent development. The mathematical model uses data from limited standard time-kill studies as inputs to capture the relationship between drug concentrations and killing rate. In conjunction with other derived model parameter estimates, such as microbial growth rate and/or adaptation tendency, comprehensive screening of efficacy and propensity to suppress resistance of a large number of dosing regimens are possible via computer simulations.

The mathematical models provided herein do not require the use of surrogate pharmacodynamic indices to make useful predictions of microbial response to antimicrobial exposures. Adaptation of a microbial population when exposed to fixed concentrations of an antimicrobial agent can be captured in a form of a mathematical model and its associated parameter estimates. The mathematical model captures the relationship between microbial burden and antimicrobial agent concentrations. A s such, the models enable a method for guiding highly targeted testing of dosing regimens, which could substantially accelerate development of antimicrobial agents. More particularly, standard time-kill studies data over 24 hours are used as model inputs. The utility of a large number of dosing regimens can be effectively screened in a comprehensive fashion, where promising regimens are investigated further in pre-clinical studies and clinical trials. It is contemplated that because the dosing regimens are designed to prevent resistance emergence, the clinical utility lifespan of new therapeutic agents or drugs would be prolonged.

The present invention provides a mathematical model comprising three parallel differential equations characterizing the rate of change of drug concentration, microbial susceptibility and microbial burden of the surviving population over time, respectively. The mathematical equations of the model predicting bacterial response to various drug exposures are as follows:

$$\frac{dC(t)}{dt} = \frac{Ro}{V} - CL \cdot C(t) \qquad \text{Eq. (I)}$$

Equation (I) describes the rate of change of antimicrobial agent concentration over time. Parameters and constants of Equation (1) include C(t) for the concentration of antimicrobial agent at time t, $R_0$ for the drug infusion rate, V for the volume of distribution, and CL for the clearance.

$$\frac{dC_{50keff}(t)}{dt} = C_{50k} \cdot \alpha \cdot \{e^{-[c(t)\cdot\tau]}\} \cdot [c(t)\cdot\tau] \qquad \text{Eq. (II)}$$

Equation (II) describes the rate of change of bacterial susceptibility to antimicrobial agent over time. Parameters and constants of Equation (2) include $C_{50keff}(t)$ for susceptibility of bacteria to antimicrobial agent, $C_{50k}$ for concentration to achieve 50% of maximal kill rate for bacterial population, $\alpha$ for maximal adaptation, and $\tau$ for the adaptation rate function.

$$\frac{dN(t)}{dt} = K_g \cdot \left[1 - \frac{N(t)}{N_{max}}\right] \cdot N(t) - \left\{\frac{C(t)^H \cdot K_k}{C(t)^H + [C_{50keff}(t)]^H}\right\} \cdot N(t) \qquad \text{Eq. (III)}$$

Equation (III) describes the rate of change of bacterial population over time. Parameters and constants of Equation (III) include N(t) for concentration of bacterial population at time t, $K_g$ is the growth rate constant for bacterial population, $N_{max}$ for the maximum population size, $K_k$ for the maximal kill rate constant for bacterial population, and H for the sigmoidicity constant for bacterial population.

Note that $C_{50keff}(t) = C_{50k} \cdot \{1 + \alpha[1 - e^{-[c(t)\cdot\tau]}]\}$. The general solution for any C(t) is:

$$\frac{dC_{50keff}(t)}{dt} = C_{50k} \cdot \alpha \cdot \{e^{-[c(t)\cdot\tau]}\} \cdot \left\{[c(t)\cdot\tau] + \left[t\cdot\tau\cdot\frac{dC(t)}{dt}\right]\right\}$$

and when C(t) is constant, the solution of the above equation is:

$$\frac{dC_{50keff}(t)}{dt} = C_{50k} \cdot \alpha \cdot \{e^{-[c(t)\cdot\tau]}\} \cdot [c(t)\cdot\tau].$$

Alternatively, in a two step process, the mathematical framework derived in Example 1 may be used to predict whether a microbial population will be eradicated or survive under an antimicrobial pressure whose concentration over time follows a clinically realistic (time-periodic) profile. In step one, short-term (24-h) time-kill data at various time-invariant concentrations of the antimicrobial agent are used and parameters values of the model that describes the effect of the agent or drug on a heterogeneous microbial population are fit using Eqs. (11), (26-28). In step two the results of step one are used to predict whether the microbial population would be eradicated or survive by focusing via Eq. (25) on D/Kg, for various dosing regimens. A dosing regimen (combination of daily dose and dosing interval) with ratio D/Kg>1, Eq. (18), is predicted to be associated with high likelihood of suppressing resistance emergence and a dosing regimen with ratio D/Kg<1 is predicted to be associated with resistance emergence.

Generally the computer simulation utilizing the mathematical model is useful to predict the long-term growth/killing of an entire microbial population exposed to an antimicrobial agent at clinically relevant concentration profiles in vitro and in vivo. This provides a computer-implemented antimicrobial agent screening methodology and system useful to guide targeted preclinical/clinical testing of antimicrobial agents, thereby resulting in significant acceleration of the antimicrobial agent development process.

Thus, the present invention provides a computer-implemented pharmacokinetic and/or screening simulation tool which uses the mathematical models described herein. As is known and standard in the art an input/output system provides a user interface between the user of the computer-implemented tool and a computer system comprising the necessary components to run the simulation, e.g., a memory storing the simulation tool and instructions, a processor to execute the simulation tool and other instructions, and a simulation engine. One of ordinary skill in the art would easily be able to provide a computer system with the necessary components, hardware and software to implement the computer simulation.

The computer-implemented system is adapted for high-throughput screening for antimicrobial agents effective to suppress emergence of acquired resistance thereto in a microbial population. Generally, the computer-implemented system comprises the memory and processor for storing and executing the simulation tool for simulating growth response over a period of time of a microbial population in contact with the antimicrobial agent, which may be the computer simulation and mathematical model described herein, an input for inputting initial parameter and constant values and an output for generating output values, as described herein, and a module or other means for correlating the output values with a likelihood of acquisition of resistance within the microbial population. In addition, and optionally, the system may further comprise a module or other means for designing a pharmacologically effective dosing regimen for the microbial population. Furthermore, a module or other means for compiling a library of the antimicrobial agents and respective dosing regimens optionally is provided.

Particularly, the present invention provides a computer-implemented method to predict the likelihood of a microbial population acquiring resistance to an antimicrobial agent over time. A time period may be, but not limited to about 24 hours. During the computer simulation, initial parameter values and constants which are operably linked to the three differential equations comprising the mathematical model are entered as input. The initial parameter values are useful to determine at least microbial susceptibility to the antimicrobial agent and growth of a microbial population during contact therewith over the period of time. Output values may be generated during the simulation predicting microbial susceptibility and microbial growth at incremental points over the time period. The likelihood of the microbial population acquiring resistance of to the antimicrobial agent is predicted based on a decrease in microbial susceptibility output values and an increase in microbial population growth output values in the microbial population which initially demonstrated susceptibility to the antimicrobial agent at or near the end of the time period which is a positive correlator with resistance acquisition. Furthermore, this method of predicting likelihood of acquiring resistance and the computer simulation and mathematical model may be adapted for methods for high-throughput screening for antimicrobial agents effective to suppress emergence of acquired resistance in a microbial population.

As such the present invention further provides for designing a dosing regimen that is pharmacologically effective against a microbial population based on the output values over the time period of the mathematical model. Furthermore, a library comprising the screened antimicrobial agents and the associated designed dosing regimens may be compiled.

In addition, the designed dosing regimens may be used to treat or prevent in a subject a pathophysiological condition caused by the microbial population for which the dosing regimen was designed. Routes of administration of an antimicrobial agent and pharmaceutical compositions, formulations and carriers thereof are standard and well-known in the art. They are routinely selected by one of ordinary skill in the art based on, inter alia, the type and status of the pathophysiological condition, whether administration is for therapeutic or prophylatic treatment, and the subject's medical and family history.

Also, provided herein is a particular method for suppressing emergence of acquired resistance of a microbial population to an antimicrobial agent useful for treating a pathophysiological condition associated therewith in a subject. A pharmacologically effective amount of an antimicrobial agent may be administered using a dosing regimen determined via the computer simulation tool described herein. The computer simulation is adapted to input parameter values into a mathematical model to determine at least microbial susceptibility to the antimicrobial agent and growth of a microbial population during contact therewith over the period of time and to generate output values predicting microbial susceptibility and microbial growth at incremental points over the time period.

Antimicrobial agents of the present invention may include antibacterials, antifungals and antivirals. It is contemplated that this model and methodology may be applied to pathogens, such as, but not limited to, Gram-positive bacteria, e.g., *Streptococcus pneumoniae* and *Staphylococcus aureus*, Gram-negative bacteria, e.g., *Escherichia coli, Klebsiella pneumoniae, Pseudomaonas aeruginosa*, and *Acinetobacter baumannii*, and other organisms or viruses, such as, yeast, molds, mycobacteria, viruses, e.g., HIV and avian influenza, and infectious agents implicated in bioterrorism, for example, but not limited to *Bacillus anthracis*. The pathophysiological conditions may be any such condition associated with or caused by a microbial population. Particularly, the pathophysiological condition may be a nosocomial infection.

It is contemplated that the systems and methods provided herein are also effective against a malignant pathophysiological condition, such as a cancer. As is well known in the art, a cancer comprises a proliferating population of malignant cells and, as with a microbial population associated with a pathophysiological condition, a tumor cell population in the absence of treatment will grow overtime, eventually killing a subject having the cancer. Medical treatment, in terms of antimicrobial or chemotherapeutics is intended to disrupt the natural growth rate or to induce killing of the microbial population or tumor cell population. The same set of problems, e.g., combinatorily large number of variables involved, trial and error approach in drug development, drug resistance upon sub-optimal treatment, etc., arises in designing a dosing regimen for antimicrobial or chemotherapeutic treatments. Thus, the computer simulation and mathematical model provided herein may be applied to chemotherapeutic agents or potential chemotherapeutic agents in the treatment of cancer.

The following example(s) are given for the purpose of illustrating various embodiments of the invention and are not meant to limit the present invention in any fashion.

EXAMPLE 1

Homogenous Microbial Population Under Time-Invariant Agent Concentration

A homogeneous microbial population in an environment of an antimicrobial agent at concentration $C(t)$ satisfies the mass balance equation $$\frac{dN}{dt} = \underbrace{K_g N(t)}_{\text{physiological growth rate}} - \underbrace{r(C(t))N(t)}_{\text{kill rate due to agent}}, N(0) = N_0 \qquad \text{Eq. (1)}$$

where $N(t)$ is the total number of bacteria at time t; $K_g$ is the physiological growth rate per unit of the bacteria (net effect of natural bacterial growth and death); and $r(C)$ is the antimicrobial agent-induced kill rate per unit of bacteria, which is a non-decreasing function of the antimicrobial agent concentration C, usually expressed by the standard equation:

$$r(C) = K_k \frac{C^H}{C^H + C_{50}^H} \qquad \text{Eq. (2)}$$

where $K_k$ is the maximum kill rate coefficient; $C_{50}$ is the concentration at which 50% of the maximum kill rate is attained; and H is the Hill factor, indicating whether $r(C)$ is heavily inflected ($H \gg 1$) or not. For a time-invariant concentration C the standard solution of Eq. (1) is $$\ln \frac{N(t)}{N_0} = \alpha t, \qquad \text{Eq. (3)}$$

indicating an exponentially growing, declining, or constant microbial population, depending on whether $\alpha = K_g - r(C)$ is positive, negative, or zero. Therefore, the value of $r(C)$ in comparison with Kg represents the microbial resistance to a specific antimicrobial agent at concentration C. The critical concentration of the antimicrobial agent, Ccr, for which a=0, i.e., $$K_g - r(C) > 0, \qquad \text{Eq. (4)}$$

is related to the standard and widely used concept of minimal inhibitory concentration (MIC), defined as the agent concentration for which the size of a microbial population at 24 h shows no visible growth (5, 14).

In reality, a growing microbial population will eventually reach a saturation value Nmax as described by the logistic growth equation (20). While Eq. (5) is more accurate than Eq. (1) for values of N near Nmax, Eq. (1) is acceptable for N Nmax, which is the focus herein.

Heterogenous Microbial Population Under Time-Invariant Agent Concentration

Unlike what Eq. (3) indicates, $\log(N(t))$ hardly ever depends linearly on t for real microbial populations. Most notably, initial decline of $N(t)$ may be followed by later regrowth. For time-invariant agent concentration, such behavior is due to the fact that microbial populations are heterogeneous, consisting of subpopulations with differing degrees of antimicrobial resistance corresponding to different kill rate coefficients $r_i(C)$ at a given antimicrobial concentration C. It is customary to lump sub-populations with $r_i(C)<Kg$ into one resistant subpopulation and the remaining sub-populations, with $ri(C)\geq Kg$, into one susceptible sub-population. Equation (1) is then applied to each of the two sub-populations. While this approach is conceptually appealing and computationally simple, it is only a rough approximation of the real system and may fail to predict phenomena such as regrowth (18). To account for this a mathematical modeling framework is developed to capture the effect of antimicrobial agents on heterogeneous microbial populations. This framework considers the distribution of the kill rate coefficient r(C) over a microbial population. A virtually continuous distribution approximation is reasonable, because the size of a microbial population in an infection is of the order of $10^8$-$10^9$. In this framework, the dynamics of the entire microbial population N were shown to be $$\frac{dN}{dt} = (K_g - \kappa_1(t))N(t). \qquad \text{Eq. (6)}$$

$$\frac{d\kappa_n}{dt} = -\kappa_{n+1}(t), n \geq 1. \qquad \text{Eq. (7)}$$

where $\kappa n(t)$, $n \geq 1$, are the cumulants (19) of the kill rate coefficient distribution function $f(r, t)$ at time t. Note that the first four cumulants are directly related to the average, $\mu$, variance, $\sigma^2$, skewness, $\mu_3/\sigma^3$, and kurtosis excess, $(\mu_4/\sigma^4)-3$, of the kill rate coefficient distribution, as $\kappa_1 = \mu$, $\kappa_2 = \sigma^2$, $\kappa_3 = \mu_3$, and $\kappa_4 = \mu 4 - 3\sigma^4$. Therefore, Eqs. (6) and (7) can be written as $$\frac{dN}{dt} = (K_g - \mu(t))N(t) \qquad \text{Eq. (8)}$$

$$\frac{d\mu}{dt} = -\sigma(t)^2 \qquad \text{Eq. (9)}$$

$$\frac{d\sigma^2}{dt} = -\kappa_3(t) \qquad \text{Eq. (10)}$$

Equation (8) indicates that the entire population grows or declines according to the average kill rate coefficient $\mu(t)$. Equation (9) suggests that the decline rate of the average kill rate coefficient is proportional to the spread of the kill rate over the microbial population. Finally, Eq. (10) suggests that the change rate of the spread of the kill rate depends on the initial distribution of the kill rate over the microbial population. For example, if the initial kill rate is almost normally distributed, then $\kappa_n = 0$ for $n \geq 3$, which implies that the kill rate will remain almost normally distributed with the same spread for a period of time. Certainly, it would be interesting to determine the evolution of the kill rate distribution with time for various initial distributions, particularly bimodal. This is a subject of current investigation. However, under fairly mild assumptions, Eqs. (6) and (7) can be proven (18) to yield explicit results for the population size $$\ln\left[\frac{N(t)}{N_0}\right] \approx \underbrace{\left(K_g - \mu(0) + \frac{\sigma(0)^2}{A}\right)}_{K_g - b}t + \underbrace{\frac{\sigma(0)^2}{A^2}}_{\frac{R}{A}}(e^{-At}-1) \qquad \text{Eq. (11)}$$

Average kill rate coefficient $$\mu(t) \approx \underbrace{\mu(0) - \frac{\sigma(0)^2}{A}}_{b} + \underbrace{\frac{\sigma(0)^2}{A}}_{R}e^{-At} \equiv Re^{-At} + b \qquad \text{Eq. (12)}$$

and variance of the kill rate coefficient $$\sigma(t)^2 \approx \sigma(0)^2 e^{-At} \qquad \text{Eq. (13)}$$

where $\kappa(0)$ and $\sigma(0)^2$ are the average and variance, respectively, of r(C) for the initial population, and A>0 is the decline rate for the average and variance of r(C) at a given C.

Equation (11) indicates that for the entire population to be eradicated by the agent, it is not enough that the initial average kill rate coefficient, $\mu(0)$, be larger than the growth rate constant, Kg, but it must be $b = \mu(0)-(\sigma(0)^2/A)>Kg$, namely the eventual kill rate coefficient $b = \lim \mu(t)$ from $t \to \infty$, by Eq. (12), must exceed $K_g$. The eventual kill rate coefficient, b, corresponds to the most resistant sub-population of the original population. The most resistant sub-population will eventually dominate, thus rendering the eventual population homogeneous, in agreement with the limit of Eq. (13) as $t \to \infty$. The essence of Eqs. (6) and (7), particularly when they can be simplified as in Eqs. (11) and (12), is that the entire population can be characterized without explicit description of each particular subpopulation corresponding to a certain level of resistance.

In the preceding analysis the growth rate constant, Kg, has been assumed to be the same for all sub-populations, because of common growth physiology. However, it could well be that resistant strains of a species adapt their biofitness by lowering their growth rate constant from $K_g$ to $K_g - \delta K_g$, where $\delta K_g$ refers to the biofitness cost. In that case, the above Eqs. (6)-(13) remain intact, the only notational difference being that all cumulants refer to the kill rate coefficient r(C) plus the biofitness cost term $\delta K_g$.

Figure 1:
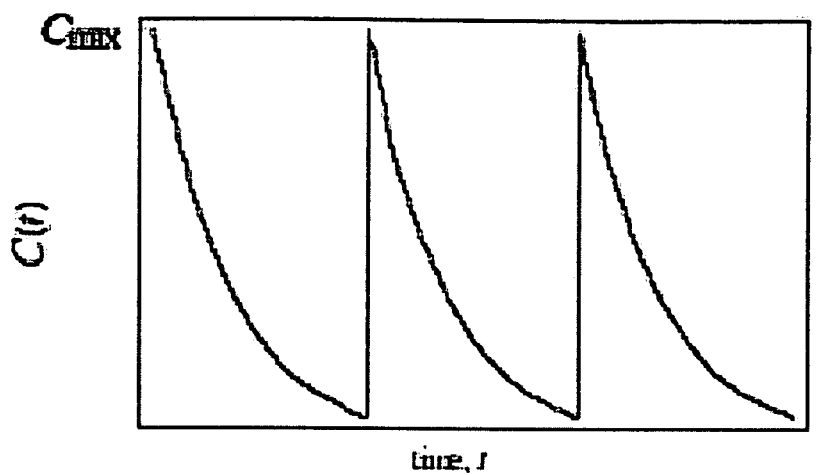

Homogeneous Microbial Population Under Time-Periodic Antimicrobial Agent Concentration Assume now that the antimicrobial agent concentration does not remain time-invariant but fluctuates periodically (due to constant elimination and periodic injections) as shown, for example, in FIG. 1. If the fluctuations have period corresponding to a dosing interval T, then $$C(t) = C(t-kT) \qquad \text{Eq. (14)}$$

The kill rate r(C(t)) corresponding to the above agent concentration will satisfy a similar periodic relationship as in Eq. 14.

Under these conditions it can be shown that the total population N(t) exhibits periodic patterns with period T, and the values of $\log(N(nT))$, $n=0, 1, 2, \ldots$, lie on a straight line, similarly to Eq. (3), as made explicit by the following Theorem 1.

Homogeneous Population Dynamics Under Time-Periodic Agent Concentration: Theorem 1

Assume that a homogeneous population of N0 bacteria satisfying Eq. (1) is subjected to periodically fluctuating antimicrobial agent concentration C(t) satisfying Eq. (14). Then, a) the bacterial population is $$\ln\left[\frac{N(t)}{N_0}\right] = K_g t - \left[\frac{t}{T}\right]DT - \int_0^{t-[\frac{t}{T}]T} r(C(\eta))d\eta \qquad \text{Eq. (15)}$$

where $$\left[\frac{t}{T}\right]$$

indicates the integer part of the real number $$\frac{t}{T},$$

and $$\boxed{D \triangleq \frac{1}{T}\int_0^T r(C(\eta))d\eta} \qquad \text{Eq. (16)}$$

is the time-averaged kill rate coefficient; and b) at times t=nT, n=0, 1, 2, . . . the total population satisfies the equation $$\ln\left[\frac{N(nT)}{N_0}\right] = (K_g - D)nT, \quad n = 0, 1, 2, \ldots . \qquad \text{Eq. (17)}$$

Figure 2A:
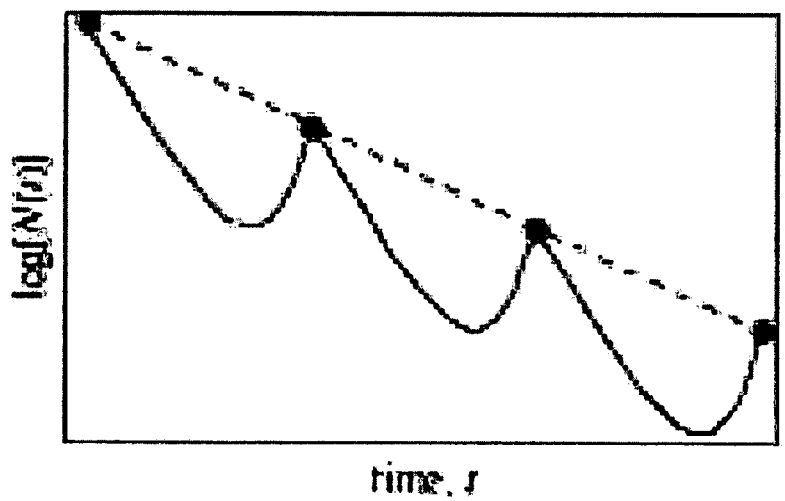
Figure 2B:
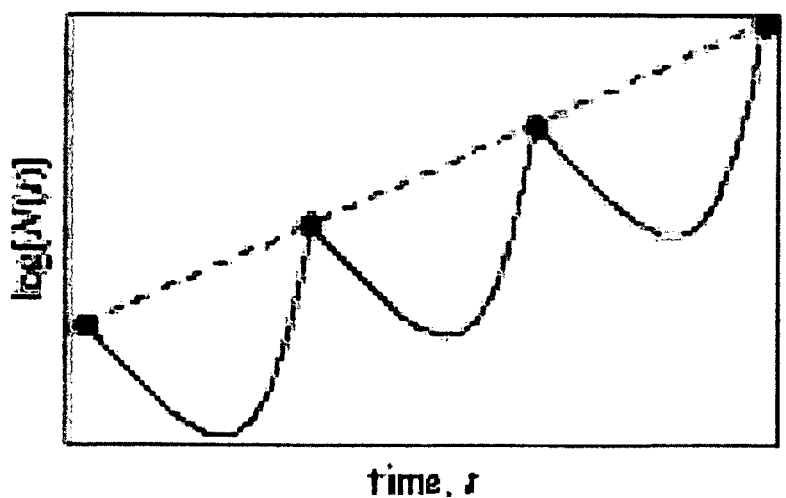
Figure 3A:
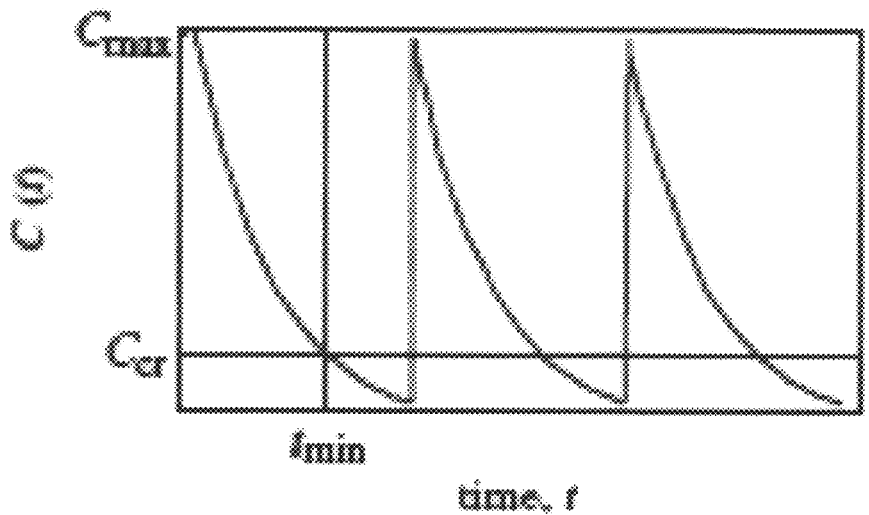
FIGS. 3A-3B depict the potential eradication of a microbial population during the first dosing interval.
Figure 3B:
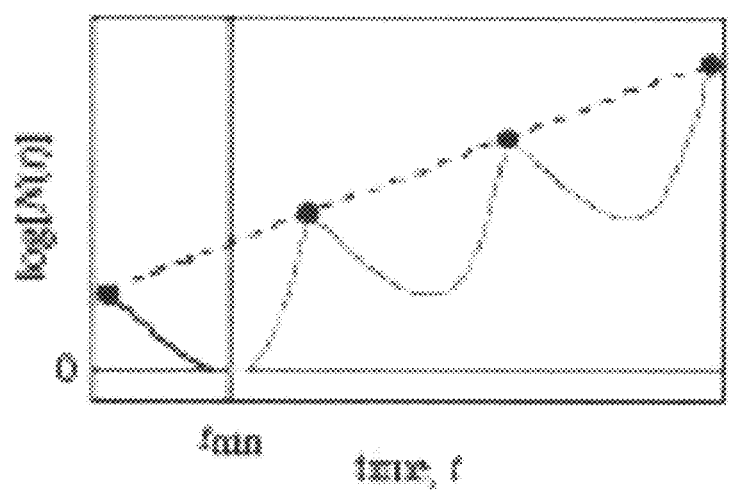
Figure 4A:
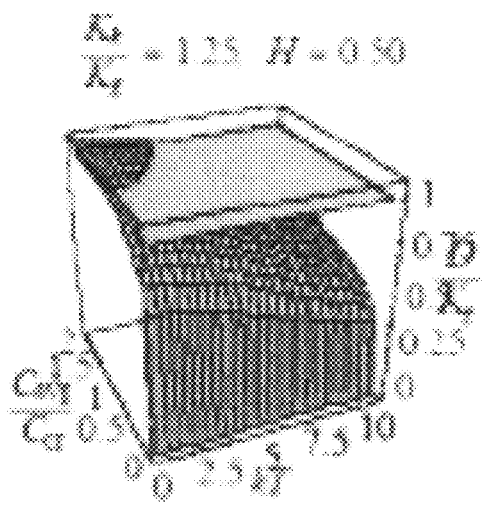
Figure 4A:
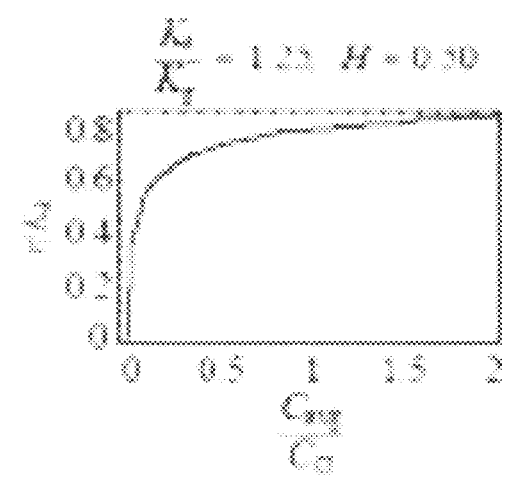
Figure 4B:
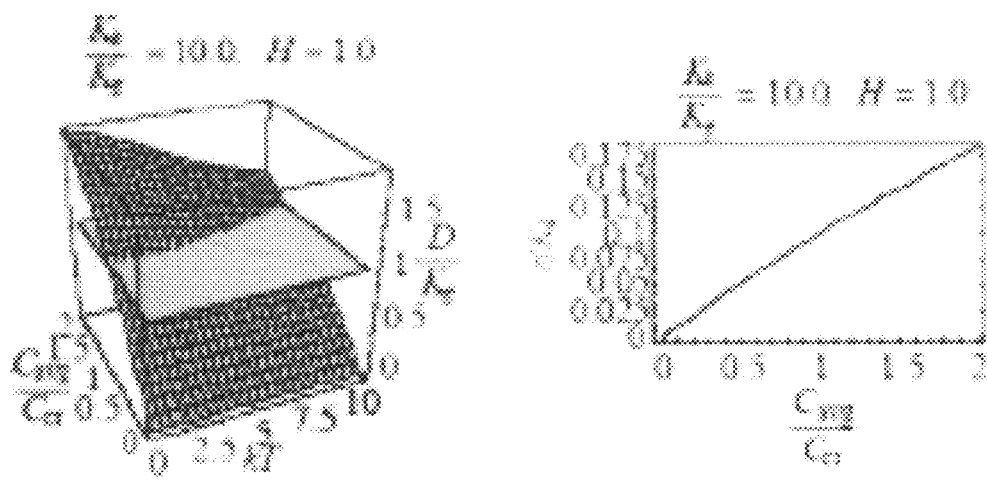
Figure 4C:
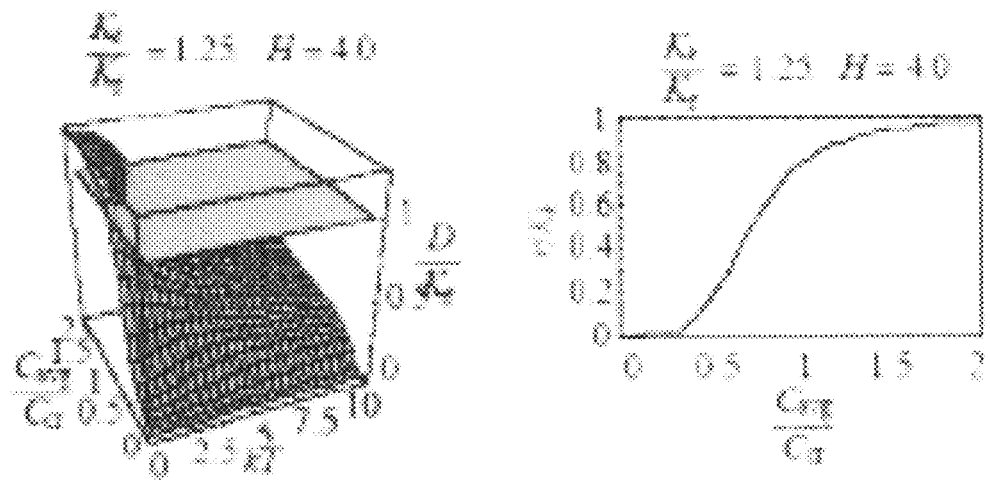
Figure 4D:
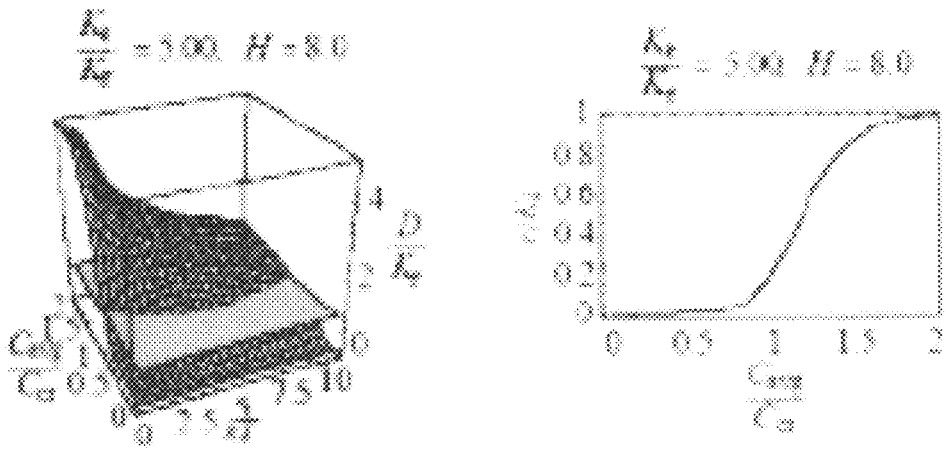

Similarly to Eq. (3) (for time-invariate agent concentration, C), Eq. (17) (for timer-periodic agent concentration C(t)) indicates that the points $\ln(N(nT)/N_o)$, n=0, 1, 2, will lie on a straight line corresponding to the time-averaged kill rate D which significantly simplifies the ensuing analysis. In other words, the points $\ln(N(nT)/N_o)$ appear as if they were generated by a system under constant agent concentration D. Therefore according to Eq. (17), $$D/Kg > 1 \qquad \text{Eq. (18)}$$

implies eradication of the entire population, whereas $D/K_g < 1$ implies eventual proliferation of the microbial population (FIGS. 2A-2B) except for the case where eradication can occur during the first dosing interval (FIGS. 3A-3B). The latter case can occur if the minimum of ln N(t), $0 \leq t \leq T$, is at or below 0. As FIGS. 3A-3B indicates, the minimum of lnN(t) occurs at time tmin, at which $$\frac{d\ln N}{dt}(t_{min}) = \frac{1}{N(t_{min})}\frac{dN}{dt}(t_{min}) = 0 \qquad \text{Eq. (19)}$$

and $$C(t_{min}) = C_{cr} \qquad \text{Eq. (20)}$$

by Eq. (4).

The conditions under which Eq. (18) is satisfied are provided as a qualitative approximate answer in the following Theorem 2 and a quantitative answer for representative pharmacokinetics/pharmacodynamics (PK/PD) in Theorem 3.

Effect of AUC/MIC on Agent Bactericidal Activity Under Realistic PK: Theorem 2

For time-periodic agent concentration corresponding to dosing interval T as in Eq. (14), the value of D/Kg is given to first-order approximation by $$\frac{D}{K_g} \approx 1 + \frac{r'(C_{cr})}{K_g}(C_{avg} - C_{cr}) \qquad \text{Eq. (21)}$$

$$= 1 + \frac{r'(C_{cr})}{K_g}C_{cr}\left(\frac{AUC/T}{C_{cr}} - 1\right)$$

where the area under the curve (AUC) is defined as $$AUC \triangleq \int_0^T C(t)dt \qquad \text{Eq. (22)}$$

Equation (21) indicates that in order to design a dosing regimen that results in bactericidal effect, the average concentration of the agent, $C_{avg}$, must be above $C_{cr}$, so that Eq. (18) hold. It is inferred from Eq. (21) that the effectiveness of an agent is approximately related to the well-known PK/PD parameter AUC/MIC≈AUC/$C_{cr}$. However, it should be stressed that the dependence of an agent's effectiveness on AUC/MIC is only approximate; if r(C) is fairly linear in the neighborhood of Ccr the approximate is reasonable. A more accurate index would have to be used to account for strong effects of higher-order derivatives in the series expansion of Eq. (21).

Theorem 3 demonstrates that if the agent concentration follows the realistic PK pattern $$C(t) = C_{max}e^{-kt}, 0 \leq t < T, \qquad \text{Eq. (23)}$$

(FIG. 1) where $k = \ln 2/t_{1/2}$ is the agent elimination rate constant (reciprocally proportional to the half-time $t_{1/2}$) and T is the dosing interval, then the value of D/Kg can be influenced by selecting two dimensionless variables associated with the dose and dosing interval of a dosing regimen, namely $z = C_{avg}/C_{cr}$ (or, equivalently, $y = C_{avg}/C_{50}$) and $x = kT$, where $$C_{avg} \triangleq \frac{1}{T}\int_0^T C(t)dt \qquad \text{Eq. (24)}$$

is proportional of the administered daily dose (mass of agent over 24 h period). It can be shown that the functional dependence of D/Kg on x, z depends on two PD parameters: H and $K_k/K_g$.

Bactericidal Effect as Function of $z = C_{avg}/C_{cr}$ and $x = kT$:
Theorem 3

Under the assumptions in Eqs. (1), (2), (23), and with D defined as in Eq. (16), then $$\frac{D}{K_g} = \qquad \text{Eq. (25)}$$

$$\frac{K_k}{K_g}\frac{1}{Hx}\ln\frac{\frac{K_k}{K_g} - 1 + \left(\frac{e^x xz}{e^x - 1}\right)^H}{\frac{K_k}{K_g} - 1 + \left(\frac{xz}{e^x - 1}\right)^H} = (1 + x_{50}^H)\frac{1}{Hx}\ln\frac{1 + \left(\frac{e^x xy}{e^x - 1}\right)^H}{1 + \left(\frac{xy}{e^x - 1}\right)^H}$$

where $$x_{50}^H \triangleq \left(\frac{C_{50}}{C_{cr}}\right)^H = \frac{K_k}{K_g} - 1,$$

$$z \triangleq \frac{C_{avg}}{C_{cr}} = \frac{dailydose \text{ [mg]}}{24 \text{ [h] clearance [L/h]}} / C_{cr},$$

$$y \triangleq \frac{C_{avg}}{C_{50}} = \frac{dailydose \text{ [mg]}}{24 \text{ [h] clearance [L/h]}} / C_{50},$$

$$x \triangleq kT = \frac{T}{t_{1/2}}\ln 2,$$

T is the dosing interval and $C_{cr}$ is defined through Eq. (4).

Equation (25) makes it clear that for a given agent, for which the values of H and $K_k/K_g$ have been estimated from preliminary experimental data, one can visualize the agent effectiveness, I.d., value of $D/K_g$, as a function of two variables that characterize a dosing regimen, namely $z = C_{avg}/C_{cr}$ and $x = kT$. FIGS. 4A-4E show a small library of such patterns for different values of H and $K_k/K_g = 1 + (C_{50}/C_{cr})^H$, along with associated plots of the scaled kill rate coefficient r(C)/Kk as a function of C/$C_{cr}$. A careful examination of these patterns for D/Kg reveals qualitatively different behaviors for different values of H and $K_k/K_g = 1 + (C_{50}/C_{cr})^H$. FIGS. 4A-4E quantifies Vogelman and Graig's well-known classification of antimicrobial agents into two broad categories, characterized according to whether agent activity is gradually or steeply concentration-dependent.

Heterogeneous Microbial Population Under Time-Periodic Antimicrobial Agent Concentration As discussed for heterogeneous microbial populations and time-invariant agent concentration above, realistic microbial populations are heterogeneous, in that not all parts of a population are killed by an agent at the same rate. Therefore, to characterize the entire population as a function of time one should follow each subpopulation using an equation analogous to Eq. (1) with time-periodic C(t). This task would be straightforward to accomplish numerically, if the initial distribution of kill rates and corresponding parameters were known. Unfortunately, such knowledge would be unavailable for all practical purposes. In addition, a lumping analytical description, akin to Eqs. (6) and (7), would be challenging as well. While such an analytical description would be worth pursuing on its own merit from the viewpoint of a mathematical biology, what is of interest from a therapeutic viewpoint is not the exact behavior of the population at all times, but rather its eventual behavior, namely whether the population will eventually be eradicated or survive. It is clear that to rigorously characterize the eventual behavior of the entire population it is necessary and sufficient to track its most resistant sub-population. This task can be accomplished as follows:

For a heterogeneous population subjected to a number of time-invariant agent concentrations C, Eq. (12) indicates that the population-average kill rate coefficient will eventually reach a value b for each C. This C-dependent kill rate coefficient, b(C), corresponds to the most resistant sub-population, which will eventually dominate the entire population, and which is homogeneous, as suggested by Eq. (13) when t→∞. Therefore, it is reasonable to assume that the functional dependence of b on C follows Eq. (2), namely $$b(C) = K_b \frac{C^{H_b}}{C^{H_b} + C_{50b}^{H_b}}. \quad \text{Eq. (26)}$$

Similarly, Eq. (12) suggests that the average kill rate coefficient at time t=0 is R+b. It has been demonstrated previously that it is reasonable to assume that the initial average kill rate coefficient depends on C in a way similar to Eq. (2), namely $$R(C) + b(C) = \quad \text{Eq. (27)}$$

$$K_k \frac{C^H}{C^H + C_{50}^H} \Rightarrow R(C) = K_k \frac{C^H}{C^H + C_{50}^H} - K_b \frac{C^{H_b}}{C^{H_b} + C_{50b}^{H_b}}.$$

Finally, it is reasonable to assume that the constant A, corresponding to the rate of decline of the kill rate coefficient with respect to time depends on C as $$A(C) = K_A \frac{C^{H_A}}{C^{H_A} + C_{50A}^{H_A}}. \quad \text{Eq. (28)}$$

Therefore, if experimental data are available from time-kill studies (measurements of population size at various sampling points in time, for a number of time-invariant concentrations C), then the parameters involved in Eq. (11) after the expressions for b, R, and A are substituted from Eqs. (26), (27), and (28), respectively can be identified. Then, predictions can be made for the effectiveness of a dosing regimen according to Eq. (25).

Proof of Theorem 1

Equation (1) implies $$N(t) = N_0 \exp\left(\int_0^t \underbrace{[K_g - r(C(\theta))]d\theta}_{\rho(\theta)}\right). \quad \text{Eq. (29)}$$

The integral in Eq. (29) can be written as $$\int_0^t \rho(\theta)d\theta = \sum_{j=0}^{n-1} \int_{jT}^{(j+1)T} \rho(\theta)d\theta + \int_{nT}^{t} \rho(\theta)d\theta \quad \text{Eq. (30)}$$

$$= \sum_{j=0}^{n-1} \int_{jT}^{(j+1)T} \rho(\theta - jT)d\theta + \int_{nT}^{t} \rho(\theta - kT)d\theta$$

$$= \sum_{j=0}^{n-1} \int_0^T \rho(\eta)d\eta + \int_0^{t-nT} \rho(\eta)d\eta$$

$$= [K_g - D]nT + K_g(t - nT) + \int_0^{t-nT} r(C(\eta))d\eta$$

which implies Eq. (15). Substitution of t by nT in Eq. (30) immediately yields the result.

Proof of Theorem 2

Equation (16) implies $$\frac{D}{K_g} = \frac{1}{K_g T} \int_0^T r(C(t))dt$$

$$\approx \frac{1}{K_g} \frac{1}{T} \int_0^T [r(C_{cr}) + r'(C_{cr})(C(t) - C_{cr})]dt$$

$$= \frac{1}{K_g}[K_g + r'(C_{cr})(C_{avg} - C_{cr})]$$

$$= 1 + \frac{r'(C_{cr})}{K_g}(C_{avg} - C_{cr})$$

$$= 1 + \frac{r'(C_{cr})}{K_g}C_{cr}\left(\frac{AUC/T}{C_{cr}} - 1\right).$$

Proof of Theorem 3

Substitution of Eq. (23) into Eq. (16) and integration yields $$\frac{D}{K_g} = \frac{K_k}{K_g HT} \ln \frac{C_{50}^H + C_{max}^H}{C_{50}^H + C_{max}^H \exp[-kTH]}. \quad \text{Eq. (31)}$$

Using Eq. (23) in Eq. (24) yields $$C_{avg} \triangleq \frac{1}{T} \int_0^T C(\eta)d\eta = \quad \text{Eq. (32)}$$

$$C_{max} \frac{1}{kT}(1 - \exp[-kT]) \Rightarrow C_{max} = C_{avg} \frac{kT}{(1 - \exp[-kT])}$$

Substitution of Eq. (32) into Eq. (31) yields Eq. (25) a immediately upon substitution of equivalent Eq. (33)

$$\frac{D}{K_g} = \frac{K_k}{K_g HT} \ln \frac{C_{50}^H + C_{max}^H}{C_{50}^H + C_{max}^H \exp[-kTH]}. \quad \text{Eq. (33)}$$

To get Eq. (25)b immediately $$K_g - r(C_{cr}) = 0 \Rightarrow z = y\left(\frac{K_k - K_g}{K_g}\right)^{1/H} \quad \text{Eq. (34)}$$

which yields the result by substitution of equivalent Eq. (34).

EXAMPLE 2

Methods and Materials

Antimicrobial Agents

Meropenem powder was obtained from AstraZeneca (Wilmington, Del.). Levofloxacin was obtained from Johnson and Johnson Pharmaceutical Research and Development, LLC (Raritan, N.J.). Gentamicin powder was obtained from Sigma (St. Louis, Mo.). Amikacin powder was obtained from LKT Laboratories, Inc. (St. Paul, Minn.). A stock solution of each drug (1024 µg/ml) in sterile water was prepared, aliquoted, and stored at −70° C. Prior to each susceptibility testing, an aliquot of the drug was thawed and diluted to the desired concentrations with cation-adjusted Mueller-Hinton broth (Ca-MHB) (BBL, Sparks, Md.).

Microorganisms

*Pseudomonas aeruginosa* standard wild-type strain ATCC 27853 and *A. baumannii* (American Type Culture Collection, Rockville, Md.) were used in the study. The bacteria were stored at −70° C. in Protect® (Key scientific products, Round Rock, Tex.) storage vials. Fresh isolates were sub-cultured twice on 5% blood agar plates (Hardy Diagnostics, Santa Maria, Calif.) for 24 hours at 35° C. prior to each experiment.

Five strains of *S. aureus* are used. Standard wild-type strain ATCC 29213 (American Type Culture Collection, Manassas, Va.) and four clinical isolates (two oxacillin susceptible [strains 55 and 60] and two oxacillin resistant [strains 25 and 62]) were used. All clinical isolates of *S. aureus* used were wild type and were found to be clonally unrelated, as determined by randomly amplified polymorphic DNA testing (19).

For the in vivo murine model, *P. aeruginosa* ATCC 27853 and its isogenic daughter strain with reduced susceptibility to meropenem (MR1—a spontaneous mutant with outer membrane porin loss but no significant over-expression of MexAB-OprM) are used. Outer membrane porin loss of MR1 was confirmed by susceptibility profiling and SDS-PAGE, as described previously (20). The bacteria were stored at −70° C. in Protect® (Key scientific products, Round Rock, Tex.) storage vials. Fresh isolates were sub-cultured twice on 5% blood agar plates (Hardy Diagnostics, Santa Maria, Calif.) for 24 hours at 35° C. prior to each experiment.

Susceptibility Studies

Minimum inhibitory concentration (MIC)/minimum bactericidal concentration (MBC) were determined in Ca-MHB using a modified macrobroth dilution method as described by the CLSI (10). The final concentration of bacteria in each macrobroth dilution tube was approximately $5 \times 10^5$ cfu/ml of Ca-MHB. Serial twofold dilutions of meropenem were used. The minimum inhibitory concentration was defined as the lowest concentration of drug that resulted in no visible growth after 24 hours of incubation at 35° C. in ambient air. Samples (50 µl) from clear tubes and the cloudy tube with the highest drug concentration were plated on Mueller-Hinton agar (MHA) plates (Hardy Diagnostics, Santa Maria, Calif.). The minimum bactericidal concentration (MBC) was defined as the lowest concentration of drug that resulted in 99.9% kill of the initial inoculum. Drug carry-over effect was assessed by visual inspection of the distribution of colonies on media plates. The studies were conducted in duplicate and repeated at least once on a separate day.

The MIC/MBC of the *P. aeruginosa* isolate to meropenem are each 1 µg/ml, respectively. The MIC/MBC of the *P. aeruginosa* isolate to gentamicin are each 2 mg/l, respectively. The MIC of the *A. baumannii* isolate to amikacin is 4 mg/l and the MBC is 8 mg/l. In vivo, the MIC of the wild-type and OprD⁻ isolates to meropenem were 1 mg/l and 4 mg/l, respectively.

Time-Kill Studies—Modeling

Time-kill studies were conducted with different and escalating meropenem concentrations. Six clinically achievable concentrations of meropenem were used, normalized to 0 (control), 0.25, 1, 4, 16 and 64 MIC. An overnight culture of the isolate was diluted 30-fold with pre-warmed Ca-MHB and incubated further at 35 8 C until reaching late log phase growth. The bacterial suspension was diluted with Ca-MHB accordingly based on absorbance at 630 nm; 15 mL of the suspension was transferred to 50 mL sterile conical flasks each containing 1 mL of an antimicrobial agent solution at 16 the target concentration. The final concentration of the bacterial suspension in each flask was $1 \times 10^8$ cfu/mL. The high inoculum used was to simulate the bacterial load in severe infection, and to allow resistant sub-population(s) to be present at baseline. The experiment was conducted for 24 h in a shaker water bath set at 35 8 C. Serial samples in duplicate were obtained from each flask over 24 h, at 0 (baseline), 2, 4, 8, 12, and 24 h, to characterize the effect of various meropenem concentrations on the total bacterial population. Prior to culturing the bacteria quantitatively, the bacterial samples (0.5 mL) were centrifuged at 10000 g for 15 min, and reconstituted with sterile normal saline to their original volumes in order to minimize drug carry-over effect. Total bacterial populations were quantified by spiral plating 10 serial dilutions of the samples (50 mL) onto MHA plates. The media plates were incubated in a humidified incubator (35 8 C) for 18-24 h, and the bacterial density from each sample was determined by CASBA-4 colony scanner/software (Spiral Biotech, Bethesda, Md., USA). The theoretical lower limit of detection was 400 cfu/mL.

Time-Kill Studies Simulating Nosocomial Infections

Time-kill studies data over 24 hours have been reported previously (21). A clinically relevant (achievable) concentration range of drug (0-64 µg/ml) was used. A dense baseline inoculum (approximately $2 \times 10^8$ cfu/ml) was used to simulate the bacterial load in severe nosocomial infections. The data were used as inputs to derive the best-fit model parameter estimates, as previously described. Overall, the observed bacterial burdens over time (under constant antimicrobial agent concentrations) were reasonably described and predicted by the mathematical model.

Hollow-Fiber Infection Model

The computer simulations were compared to experimental data from an in-vitro hollow fiber infection model with similar antimicrobial agent exposures (20). Basically the drug was injected directly into the central reservoir to achieve the peak concentration desired. Fresh (drug-free) growth medium (Ca-MHB) was continuously infused from the diluent reservoir into the central reservoir to dilute the drug in order to simulate drug elimination in humans. An equal volume of meropenem-containing medium was removed from the central reservoir concurrently to maintain an isovolumetric system. Bacteria were inoculated into the extracapillary compartment of the hollow-fiber cartridge (Fibercell Systems, Inc., Frederick, Md.); they are confined in the extracapillary compartment, but are exposed to the fluctuating drug concentration in the central reservoir by means of an internal circulatory pump in the bioreactor loop. The optional absorption compartment of the system was not used.

Bioassay

Drug concentrations were determined by a microbioassay utilizing *Klebsiella pneumoniae* ATCC 13883 as the reference organism. The bacteria were incorporated into 30 mL of molten Ca-MHA (at 50° C.) to achieve a final concentration of approximately 1×10⁵ CFU/mL. The agar was allowed to solidify in 150 mm media plates. Size #3 cork-bore was used to create nine wells in the agar per plate. Standards and samples were tested in duplicate with 40 IL of the appropriate solution in each well on the same day. The media plates were incubated at 35° C. for 24 h and the zones of inhibition were measured. The assay was linear (correlation coefficient≧0.99) using zone diameter versus log of the standard drug concentration.

The levofloxacin standard solutions ranged from 0.5 to 64 Ig/mL in Ca-MHB. The intraday and interday coefficients of variation (CV) for all standards were <2% and <10%, respectively. The gentamicin standard solutions ranged from 1 to 32 mg/l in Ca-MHB. The intraday and interday coefficient of variation (% CV) for all standards were <4% and <6%, respectively.

Similarly, amikacin concentrations were determined by a microbioassay utilizing *Escherichia coli* ATCC 25922 as the reference organism. The assay was linear (correlation coefficient≧0.98) using zone diameter versus log of the amikacin standard concentrations from 4-256 mg/l. The intraday and interday coefficient of variation (% CV) for all standards were <7% and <12%, respectively.

In vivo meropenem concentrations in mouse serum were determined by a microbioassay utilizing *Escherichia coli* ATCC 25922 as the reference organism. The meropenem standard solutions ranged from 0.5 to 128 μg/ml in mouse serum. The assay was linear (correlation coefficient≧0.97) using zone diameter versus log of the standard drug concentration. The intraday and interday coefficient of variation (% CV) for all standards were <4% and <5%, respectively.

Animals

Female Swiss-Webster mice (22-26 g) were used; all mice were cared for in accordance to the highest humane and ethical standards, as approved by the Institutional Animal Care and Use Committee (IACUC). The animals were housed in isolation boxes to decrease the risk of infection from extraneous pathogens. They received food and water ad libitum. The animals were rendered neutropenic by 2 intra-peritoneal injections of cyclophosphamide (Sigma, St. Louis, Mo.) 150 mg/kg on day −4 and 100 mg/kg on day −1 prior to infection; previous studies have shown that this regimen would produce neutropenia for 5 days (13, 16). Transient nephrotoxicity was induced by 1 intra-peritoneal injection of uranyl nitrate (5 mg/kg on day −2), which has been previously shown to produce a significant stable reduction in renal function for at least 7 days (21).

EXAMPLE 3

Modeling Time-Kill Studies

*P. aerugenosa* and *meropenem*

Time-Kill Studies

The time courses of bacterial burden associated with various meropenem concentrations were as shown in FIG. 5A. There was a significant (>2 log) drop in bacterial burden at 24 h with meropenem concentrations 4 MIC (4 mg/L). Meropenem exhibited a partially concentration-dependent killing profile; initial killing of meropenem appeared to have been maximized at a concentration of 4 MIC. These observations are consistent with previous in vitro studies with the β-lactams. Regrowth was observed with meropenem concentrations of 0.25 MIC and 1 MIC between 12 and 24 h. The bacterial burden observed at 24 h was modelled using an inhibitory sigmoid Emax model (conventional approach) (FIG. 5B).

Growth Dynamics Model

The time courses of bacterial burden under different drug exposures is described using a mathematical model. The population balance for a bacterial population is determined by: Rate of change of bacterial population over time=intrinsic growth rate−kill rate by antimicrobial agent or $$\frac{dN(t)}{dt} = G[N(t)] - K[C(t), N(t)] \qquad \text{Eq. (35)}$$

where $$G[N(t)] = K_g \cdot \left[1 - \frac{N(t)}{N_{max}}\right] \cdot N(t)$$

$$K[C(t), N(t)] = \left[\frac{C(t)^H \cdot K_k}{C(t)^H + (\alpha \cdot C_{50k})^H}\right] \cdot N(t)$$

and $K_g$—growth rate constant for bacterial population;
$N(t)$—concentration of bacterial population at time t;
$N_{max}$—maximum population size;
$C(t)$—concentration of meropenem at time t;
$K_k$—maximal kill rate constant for bacterial population by meropenem;
H—sigmoidicity constant for bacterial population;
α—adaptation function; and $$\alpha = 1 + \beta[1 - e^{-c(t) \cdot L \cdot \tau}] \qquad \text{Eq. (36)}$$

β—maximal adaptation;
τ—rate of adaptation factor.

In contrast to the conventional approach in which the final observed effects are modelled, information over time was utilized to develop a dynamic model system that would capture bacterial growth/killing rates. The starting point was a mathematical model describing the time course of bacterial burden [biological response, N(t)] under the influence of various antimicrobial agent concentrations C(t). The rate of change of bacteria over time was expressed as the difference between the intrinsic bacterial growth rate and the kill rate provided by the antimicrobial agent (Eq. 35). Based on previous studies, a linear bacterial growth rate was adopted. Additional model parameters were used to account for other physiological phenomena such as contact inhibition (using a maximum population size) and non-linear (sigmoidal) kill rate to account for target site saturation. Regrowth was attributed to adaptation, which was explicitly modelled as increase in the concentration necessary to achieve 50% maximal kill rate ($C_{50k}$), using a saturable function of antimicrobial agent selective pressure (both meropenem concentration and time) (Eq. 36).

The experimental data derived from the time-kill studies were analysed by population analysis, using the non-parametric adaptive grid (NPAG) program (28). The killing profile observed with each meropenem concentration was input as a subject in the population analysis. The search algorithm sought the combination of parameter values and their distributions that would have the highest likelihood of explaining the observations made with all the meropenem concentrations in a single step (as opposed to fixing some parameter estimates sequentially while estimating the others). The explicit assumption was made that overall observation variance was proportional to variance of the measurement, i.e. quantitative cultures. The proportionality constant g was optimized with each cycle of the analysis.

Figure 6A:
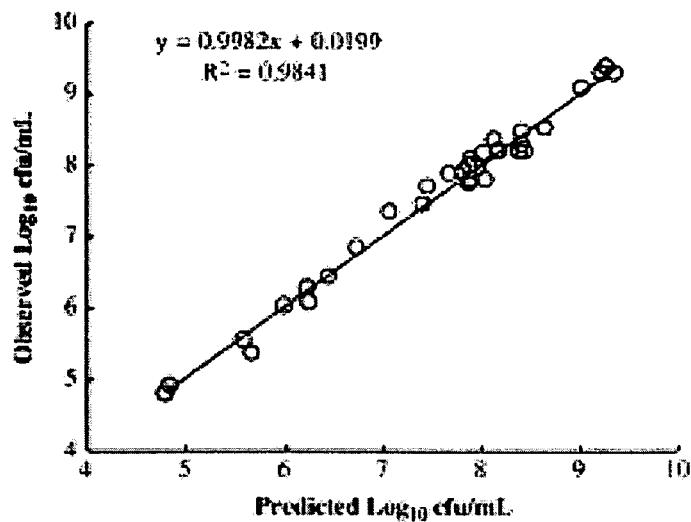
FIGS. 6A-6C show the MAP Bayesian predictions of bacterial burden based on mean parameters of the best-fit model (FIG. 6A), and demonstrate the relationship between bactericidal activity and concentration of meropenem (FIG. 6B) and the relationship between adaptation (increase in $C_{50k}$) and time with various meropenem concentrations (FIG. 6C).
Figure 6B:
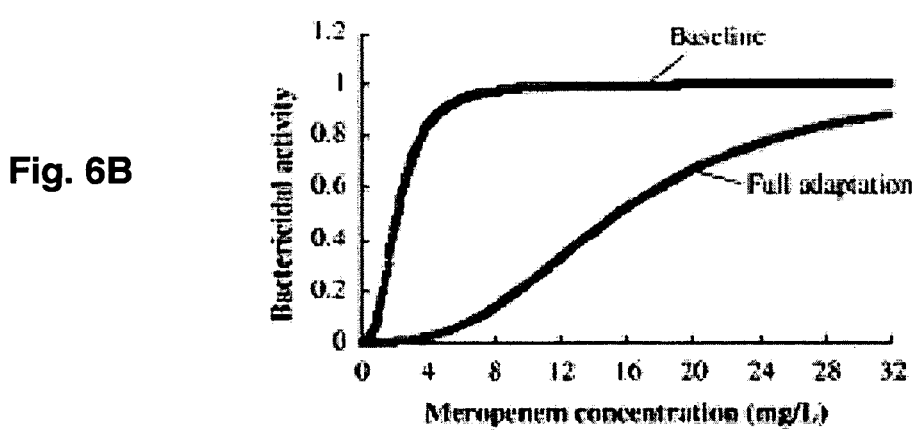
Figure 6C:
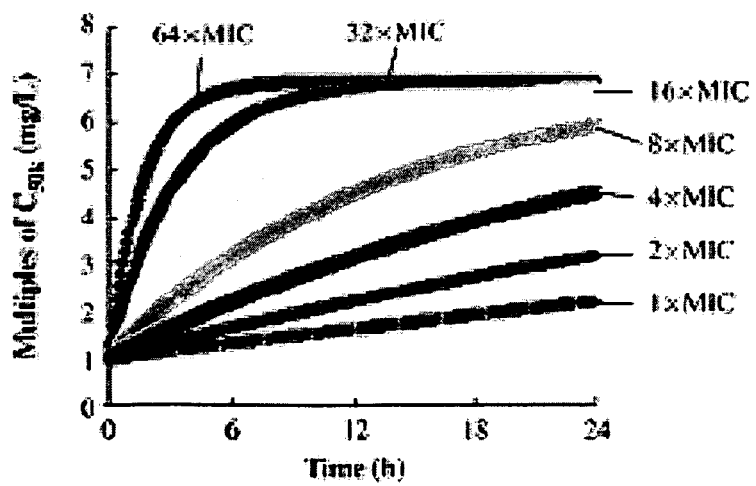

The final best-fit model consisted of eight parameters. The final estimates of the parameters and their SDs are as shown in Table 1. The model fit to the data was satisfactory; $r^2$ of MAP Bayesian predictions based on the mean parameter estimates was 0.984 (FIG. 6A). At baseline, the concentration necessary to attain 80% maximal kill rate (C80k) and 90% maximal kill rate (C90k) was achieved with meropenem at 3.8 and 5.0 mg/L, respectively (FIG. 6B). As the surviving bacterial population became more resistant (adapted) over time, a higher concentration was needed to achieve the same kill rate. The rate of adaptation (increase in C50k) over time was as shown in FIG. 6C, as a function of meropenem concentration and time (selective pressure). Faster adaptation was observed with higher meropenem concentrations, as anticipated.

TABLE 1

| Concn (mq/L) | Kg (h − 1) | Kg (h − 1) | Ck50 (mq/L) | H |
|---|---|---|---|---|
| 0 | 0.31 | 4.08 | 3.53 | 1.48 |
| 0.25 | 0.61 | 9.60 | 0.44 | 3.81 |
| 1 | 0.31 | 4.08 | 3.53 | 1.48 |
| 4 | 2.31 | 3.12 | 0.74 | 1.67 |
| 16 | 2.85 | 3.41 | 2.61 | 7.74 |
| 64 | 2.58 | 3.95 | 2.90 | 0.79 |
| Mean | 1.50 | 4.71 | 2.29 | 2.83 |
| DS | 1.10 | 2.22 | 1.25 | 2.39 |

| Concn (mg/L) | Nmax ($10^8$ cfu/ml) | Inoculum ($10^8$ cfu/ml) | β | τ (L/mg.h) |
|---|---|---|---|---|
| 0 | 2.39 | 1.49 | 6.64 | 0.011 |
| 0.25 | 9.99 | 2.50 | 3.79 | 0.021 |
| 1 | 2.29 | 1.49 | 6.64 | 0.011 |
| 4 | 9.99 | 3.03 | 4.48 | 0.0069 |
| 16 | 9.99 | 2.62 | 4.85 | 0.0051 |
| 64 | 9.99 | 3.14 | 8.70 | 0.0014 |
| Mean | 7.43 | 2.37 | 5.85 | 0.0095 |
| DS | 3.64 | 0.66 | 1.66 | 0.0063 |

In Table 1, the following parameters are used: Concn, meropenem concentration; $K_g$, growth rate constant for bacterial population; $K_k$, maximal kill rate constant for bacterial population by meropenem; $C_{50k}$, concentration to achieve 50% of maximal kill rate for bacterial population; H, igmoidicity constant for bacterial population; Nmax, maximum population size; b, maximal adaptation; t, rate of adaptation factor; and SD, standard deviation.

Model Validation

To examine the robustness and predicting ability of the model, final parameter estimates from the best-fit model were used to simulate bacterial behaviours under the influence of meropenem concentrations not previously investigated, using the ADAPT II program (22). The predicted bacterial burden over time associated with a meropenem concentration was first simulated with the maximum a-posteriori probability (MAP) Bayesian estimated growth dynamics parameter of the two regimens closest to the concentration used (e.g. final parameter estimates derived for both 1 MIC and 4 MIC were used to predict the effect associated with 2 MIC). The final prediction was based on the mean of both sets of simulations.

Time-kill studies, as described in Example 2, were repeated in duplicate on different days with meropenem at 2 and 32 MIC. The observed time courses of bacteria over time were compared with the model predictions. To substantiate the physiological basis of our modelling approach, all samples in the validation time-kill studies were also cultured quantitatively on MHA plates supplemented with meropenem at 1, 2 and 4 mg/L. The distribution of susceptibility in the bacterial population was tracked over time (susceptibility distribution analysis) under the influence of meropenem, to provide an explanation of regrowth.

Model Validations

The predicted and observed time courses of the bacteria were as shown in FIGS. 7A-7B. The predictions correlated well with the observations, suggesting good predicting ability of the model. The $r^2$ between predicted and mean observed bacteria burden for 2 and 32 MIC of meropenem were 0.83 and 0.97, respectively. Despite apparently conflicting input data (regrowth was observed with meropenem at 1 MIC, but not with 4 MIC), the model accurately predicted regrowth associated with meropenem at 2 MIC. Susceptibility distribution analysis suggested that there were multiple bacterial sub-populations. The proportion of sub-populations with reduced susceptibility in the total bacterial population remained relatively constant over time in the absence of a selective pressure (placebo) (FIG. 8A). Regrowth could be explained by selective amplification of sub-populations with reduced susceptibility over time in the presence of low (at 2 MIC) meropenem exposure (FIG. 8B). All sub-populations with reduced susceptibility grew, and the surviving bacterial population became increasingly resistant over time. The entire bacterial population had an MIC of >1 mg/L at 24 h, compared with 1 in 106 cfu at baseline. With an elevated (at 32 MIC) meropenem exposure, all bacterial populations were suppressed and no regrowth was observed (FIG. 8C).

EXAMPLE 4

Modeling Time-Kill Studies

*Staphylococcus aureus* and *gentamicin*

Time-kill modeling was performed for *S. Aureus* and gentamicin as for *P. aeruginosa* according to procedures and dynamic growth modeling in Examples 2-3.

Susceptibilities and Mutation Frequencies

The susceptibilities of the bacterial isolates to gentamicin were as shown in Table 2. Baseline resistant subpopulations were detected in all isolates. The mutation frequency of gentamicin resistance (more than 3 times the MIC) ranged from 1 in $3\times10^4$ to 1 in $4\times10^5$.

TABLE 2

| *S. aureus* strain | MIC/MBC (μ/mL) | $K_g$ (h − 1) | Nmax ($10^8$ CFU/mL) | Kg (h − 1) |
|---|---|---|---|---|
| ATCC 29213 | 1/2 | 0.56 | 0.95 | 20.08 |
| 55 | 0.5/2 | 0.18 | 0.34 | 9.44 |
| 60 | 1/2 | 0.12 | 1.38 | 10.30 |
| 25 | 1/2 | 0.16 | 1.60 | 5.95 |
| 62 | 1/1 | 0.13 | 1.33 | 10.16 |

| *S. aureus* strain | C50K (mg/L) | H | β | τ (L/mg.h) |
|---|---|---|---|---|
| ATCC 29213 | 5.14 | 0.75 | 14,620 | 0.00011 |
| 55 | 2.58 | 1.07 | 166.5 | 0.00178 |
| 60 | 1.05 | 1.52 | 427.9 | 0.00277 |
| 25 | 3.18 | 1.27 | 9,952 | 0.00002 |
| 62 | 0.65 | 1.61 | 336.2 | 0.00715 |

Time-Kill Studies and Pharmacodynamic Modeling

The killing profiles of gentamicin against *S. aureus* ATCC 29213 are as shown in FIG. 9A. A consistent trend was apparent for all five *S. aureus* isolates (see the supplemental data). Overall, the bactericidal activity appeared to be concentration dependent, as gentamicin concentration was increased from 0.5 to 4 times the MIC. However, the rate of killing seemed to plateau at concentrations beyond 4 to 8 times the MIC.

The model fits to the data were satisfactory. The $r^2$ for *S. aureus* ATCC 29213, 55, 60, 25, and 62 were 0.915, 0.946, 0.942, 0.942, and 0.900, respectively (FIG. 9B). The final model parameter estimates are as shown in Table 2, and the relationships between gentamicin concentration and bactericidal activity are as shown in FIG. 9C. Against *S. aureus*, killing of the predominant bacterial population was the prominent feature observed (with minimal adaptation resulting in regrowth); the bactericidal activity observed was concentration dependent at low concentrations (less than 4 times the MIC), and further increase in killing activity became less substantial when the concentration was beyond 4 to 8 times the MIC (FIG. 9C).

Pharmacokinetic Validation and Microbiologic Responses in Hollow-Fiber Infection Models All simulated gentamicin exposures were satisfactory and the $r^2$ values for once- and three-times-daily dosing were 0.962 and 0.989, respectively (data not shown). The effect of different concentration-time profiles of gentamicin on *S. aureus* ATCC 29213 are shown in FIG. 10. Against *S. aureus*, gentamicin dosing given 3 times daily appeared to be more bactericidal compared to once-daily administration, using identical daily doses. Both dosing regimens achieved substantial killing (approximately 5-log kill) at 24 h, but regrowth was apparent with repeated dosing over the next 4 days for the once-daily dosing regimen. On the other hand, sustained bacterial suppression over 5 days was observed with the 3-times-daily dosing regimen.

EXAMPLE 5

Meropenem Activity Against *Pseudomonas aeruginosa*

Pharmacokinetic Profiles

Different dosing strategies of meropenem were investigated for their propensity to suppress resistance. A fixed maximum concentration (Cmax) resulting from a 1 g clinical dose (64 µg/ml) with repeated dosing every 8 hours (to re-attain Cmax) was used in all the dosing regimens investigated. The dosing regimens differed in the simulated elimination half-lives (1-3 hours), resulting in different concentrations at the end of the dosing interval (Cmin).

Computer Simulations

Using the best-fit model parameter values derived, microbial response to various meropenem exposures over 5 days was predicted. The three parallel differential equations described herein are used, each characterizing the rate of change of drug concentration (pharmacokinetics), microbial susceptibility and microbial burden of the surviving population over time, respectively. All simulations were performed with the ADAPT II program (22).

Hollow Fiber Infection Model

Various elimination half-lives (1-3 hours) of meropenem were simulated and were validated subsequently in the infection models. Serial samples were obtained at baseline and daily (pre-dose) in duplicate from each hollow fiber system, for quantitative culture to define the effect of various drug exposures on the total bacterial population and on selection of resistant bacterial sub-populations.

Prior to culturing the bacteria quantitatively, the bacterial samples were centrifuged at 15,000 G for 15 minutes and reconstituted with sterile normal saline in order to minimize drug carry-over effect. Total bacterial populations were quantified by spiral plating 10× serial dilutions of the samples (50 µl) onto drug-free Mueller-Hinton agar (MHA) plates (Hardy Diagnostics, Santa Maria, Calif.). Sub-populations with reduced susceptibility (resistant) were quantified by culturing onto MHA plates supplemented with meropenem at a concentration of 3×MIC of drug. Since susceptibility testing is performed in twofold dilutions and 1 tube (2× in concentration) difference is commonly accepted as reasonable interday variation, quantitative cultures on drug supplemented media plates (at 3×MIC) would allow reliable detection of bacterial sub-populations with reduced susceptibility. The media plates were incubated at 35° C. for up to 24 (total population) and 72 hours (sub-populations with reduced susceptibility), then bacterial density from each sample was estimated by CASBA-4 colony scanner/counter (Spiral Biotech, Bethesda, Md.). The theoretical lower limit of detection was 400 cfu/ml.

The pharmacokinetic simulation in the hollow fiber infection model was satisfactory (FIG. 11). The comparison between computer simulated and experimental microbial responses are as shown in FIGS. 12A-12E. Overall, the computer predictions correlated well with experimental data qualitatively with respect to eradication or regrowth due to resistance emergence. A significant initial reduction in microbial burden was predicted for all dosing regimens examined. However, regrowth over time was predicted for sub-optimal regimens with repeated dosing due to selective amplification of resistant sub-population(s). On the other hand, sustained suppression of resistance emergence was achieved with optimal dosing regimens. Using the conventional nomenclature, the computer simulations were correct in predicting that all dosing regimens with % T>MIC of <100% were associated with regrowth. In order to suppress the emergence of resistance, dosing regimens achieving Cmin/MIC≧4 would be necessary.

Meropenem Resistant *P. aeruginosa* Isolates

In order to substantiate that bacterial regrowth over time was due to emergence of resistance, the susceptibility of the resistant isolates (recovered from the drug-supplemented media plates at the end of the experiments) to meropenem was repeated. The susceptibility of these meropenem-resistant isolates to a screening panel of antimicrobial agents was also performed to provide insights on the likely mechanism(s) of resistance. Based on the phenotypic resistance profiles of the resistant isolates, the mechanism(s) of resistance was investigated using an appropriate and well-known methodology, i.e., SDS-PAGE and/or Western immunoblotting with anti-MexB antibodies, as described previously (20).

The susceptibility profiles of the resistant isolates recovered from MEM-supplemented plates are shown in Table 3. Meropenem resistance was phenotypically stable. The mechanisms of resistance were found to be deletion of outer membrane porin (OprD) protein and efflux pump (MexAB-OprM) over-expression, as reported previously (20). These data provided further molecular evidence on the emergence of resistance over time, consistent with our modeling strategy to account for regrowth.

TABLE 3

| Strain | Exposure ($C_{min}$/MIC) | MEM* (mg/L) | PIP | CAZ | IPM | LVX | TOB | CAR* | Mechanism(s) of resistance |
|---|---|---|---|---|---|---|---|---|---|
| PA 27853 | — | 1 | 3 | 1 | 3 | 0.75 | 0.5 | 64 | — |
| MR1 | Placebo | 4 | 3 | 1 | >32 | 0.75 | 0.5 | ND | OprD− |
| MR2 | 0.5 | 64 | 8 | 2 | >32 | 4 | 0.5 | 512 | OprD− & Mex+ |

TABLE 3-continued

| Strain | Exposure ($C_{min}$/MIC) | MEM* (mg/L) | PIP | CAZ | IPM | LVX | TOB | CAR* | Mechanism(s) of resistance |
|---|---|---|---|---|---|---|---|---|---|
| MR3 | 1.7 | 32 | 32 | 4 | 32 | 6 | 0.5 | 512 | OprD– & Mex+ |

*Meropenem and carbenicillin MIC determined by macrobroth method, other MIC determined by Etest

EXAMPLE 6

Activity of Levofloxin Against *Pseudomaonas aeruginosa*

Time-Kill Studies

Time-kill studies were conducted with different and escalating concentrations of levofloxacin. Nine concentrations of levofloxacin were used: 0 (control) to 64 Ig/mL. An overnight culture of the isolate was diluted 30-fold with pre-warmed Ca-MHB and incubated further at 35 C until reaching late log phase growth. The bacterial suspension was diluted with Ca-MHB accordingly based on absorbance at 630 nm; 15 mL of the suspension was transferred to 50 mL sterile conical flasks each containing 1 mL of a drug solution at 16·the target concentration. The final concentration of the bacterial suspension in each flask at baseline was approximately $1 \times 10^8$ CFU/mL.

The high inoculum was used to simulate the bacterial load in a severe infection, e.g., nosocomial pneumonia. Furthermore, the high inoculum used would allow resistant subpopulation(s) to be likely present at baseline. The experiment was conducted for 24 h in a shaker water bath set at 35° C. Serial samples (baseline, 0.5, 1, 2, 4, 8, 12, and 24 h) were obtained from each flask over 24 h to characterize the effect of various drug exposures on the total bacterial population.

Prior to culturing the bacteria quantitatively, the bacterial samples (0.5 mL) were centrifuged at 10,000 g for 15 min, and reconstituted with sterile normal saline to their original volumes in order to minimize drug carry-over effect. Total bacterial populations were quantified by spiral plating 10 serial dilutions of the samples (50 IL) onto Ca-MHA plates. The media plates were incubated in a humidified incubator (35° C. for 18-24 h, and the bacterial density from each sample was determined by CASBA-4 colony scanner/software (Spiral Biotech, Bethesda, Md.). The reliable limit of detection was 400 CFU/mL. The experiment was repeated once on a separate day.

The bactericidal activity of levofloxacin was found to be concentration-dependent. With increasing concentrations of levofloxacin used, a faster killing rate and a greater extent of killing were seen (FIG. 13). Regrowth is evident after the initial reduction in bacterial burden in almost all time-kill studies.

Model Fit to the Data

The mathematical framework described Example 1 is used to predict whether a microbial population will be eradicated or survive under an antimicrobial pressure whose concentration over time follows a clinically realistic (time-periodic) profile. For absence of agent (placebo, C=0 Ig/mL) and by inspection in FIG. 13 it is determined that Nmax=$10^{9.4}$ CFU/mL. Using this value for Nmax standard nonlinear least squares (differential evolution of mathematica) is used to get a growth rate constant value Kg=0.22 $h^{-1}$.

It is assumed that Kg is the same for all bacterial subpopulations, owing to common basic physiology. For the highest agent concentration used (C=64 Ig/mL) there appears to be complete eradication of the entire microbial population after the third sample in time. Therefore, no experimental points beyond that are considered in the data fit. Further, it is assumed that the maximum kill rate, $K_k$, occurring at an antibiotic concentration high enough to saturate all bacterial target sites, is the same for all bacteria, namely $K_k = K_b$. The value of $K_b$ is estimated from the data at C=64 Ig/mL to be $K_b = K_k = 13.5$ $h^{-1}$. The values of the remaining parameters are estimated using standard nonlinear least squares for concentrations C=0.5, ..., 32 Ig/mL (Table 4). Comparison between model fit and measurements is shown in FIGS. 14A-14C.

TABLE 4

| Parameter | Value |
|---|---|
| $K_g$ | 0.22 $h^{-1}$ |
| $N_{max}$ | $10^{9.4}$ CFU/mL |
| $K_k = K_b$ | 13.5 $h^{-1}$ |
| $C_{50}$ | 0.86 µg/mL |
| $C_{50A}$ | 0.45 µg/mL |
| $C_{50b}$ | 39.4 µg/mL |
| H | 1.7 |
| $H_A$ | 10 |
| $H_b$ | 24 |
| $K_A$ | 0.7 $h^{-1}$ |

Simulation and Hollow Fiber Infection Model

Substituting the parameter values for Kg, Kb, $C_{50b}$, and $H_b$ of Table 4 into Eq. (25), as discussed above, the three-dimensional response surface of FIG. 15 is obtained. It is evident that for a dosing interval of 24 h, a total of at least 2126 mg of a daily dose is required for eradication of the most resistant bacterial subpopulation, hence of the entire population as well. It is also evident that the daily dose of 750 mg recommended in standard literature is going to be inadequate, according to the mathematical model. These predictions were verified experimentally in the hollow fiber experimental infection model system as discussed in Example 1. Both simulated levofloxacin exposures were satisfactory ($r^2 > 0.95$), as shown in FIGS. 16A-16B.

Microbiologic Response

Placebo control did not exert a selective pressure on the bacterial population, therefore no resistant subpopulation was detected over the duration of the experiment (FIG. 17A). With the simulated clinical dose (750 mg given once daily), a significant killing of the bacterial population was observed at 4 and 8 h. However, regrowth was apparent with repeated dosing beyond 24 h, similar to that observed in time-kill studies. Regrowth observed over time was likely due to selective amplification of pre-existing resistant mutant resistant sub-population(s) likely to be present at baseline, as demonstrated in FIG. 17B. This is consistent with our modeling approach. Susceptible bacterial populations were selectively eradicated, resulting in unopposed growth of resistant sub-population(s) and consequently the enrichment of the total bacterial population by the resistant sub-population. As a proof of concept, a supra-clinical dose (3000 mg given once daily) above the threshold exposure for resistance development was simulated to verify if resistance in *P. aeruginosa* could be counter-selected. As predicted, sustained killing of the total bacterial burden and suppression of resistant sub-population was achieved over 5 days (FIG. 17C).

Levofloxacin Resistant Isolates

Bacterial isolates were recovered from levofloxacin supplemented media plates at the end of the experiment and their susceptibility to levofloxacin was repeated to confirm the presence of resistance (to rule out degradation of drug supplementation in Ca-MHA resulting in detecting falsely resistant isolates). To provide insights on the mechanism(s) of levofloxacin resistance and cross resistance to other agents, susceptibilities of the resistant isolates were also repeated using a screening panel of antimicrobial agents (consisting of ciprofloxacin, cefepime, imipenem, meropenem, and tobramycin).

Based on the resistant phenotypic profiles, the quinolone resistance determining regions (QRDR) of genes encoding for the topoisomerases (gyrA and parC) were amplified by polymerase chain reaction (PCR), using primers and thermocycling conditions as described previously (23). The genetic sequences of the PCR products were subsequently determined with both primers (forward and reverse sequences), using the ABI 3730 XL DNA analyzer (Applied Biosystems, Foster City, Calif.) and compared to the parent strain to detect point mutations) resulting in amino-acid residue substitution(s). The wild type PAO1 sequences (GenBank accession numbers L29417 (gyrA) and AB003428 (parC)) were also used for comparison.

Two random isolates were recovered from drug supplemented media plates; they were both found to have 16-fold increase in MIC to levofloxacin, compared to the parent strain. Significant cross resistance ($\geq 4$ fold change in MIC) to other antimicrobial agents in the screening panel was not observed (except for ciprofloxacin), suggesting mutation in QRDR of genes encoding for the topoisomerases was most likely to be involved (compared to efflux pumps over-expression). PCR and sequencing studies of the parent strain and PAO1 were identical in the QRDR of gyrA and parC. Both levofloxacin resistant isolates revealed point mutations resulting in amino-acid changes in the QRDR of gyrA (T83I), but not in parC, consistent with a common genotype associated with quinolone resistance in clinical strains of *P. aeruginosa*.

EXAMPLE 7

Activity of Gentamicin Against *Pseudomaonas aeruginosa* and of Amikacin Against *Acinetobacter baumannii*

Time-Kill Studies

A clinical relevant concentration range of gentamicin (from 0-32 mg/l) was used. Similarly, the experiment was repeated with *A. baumannii* using a clinical relevant concentration range of amikacin (from 0-128 mg/l). The data were used as inputs to derive the best-fit model parameter estimates, as previously described (24, 17). The baseline inoculum ($10^7$ CFU/ml) was deemed to be dense enough to constitute a heterogeneous bacterial population. Data from the time-kill studies and model fits to the data are as shown in FIGS. 18A-18B and FIGS. 19A-19B, respectively. The estimates of the best-fit model parameters are as shown in Table 5. Taken as a whole, the observations in bacterial burdens over time, under constant antimicrobial agent concentrations, were reasonably described by the model. In Table 5: PA—*P. aeruginosa*, AB—*A. baumannii*, Kg—growth rate constant for bacterial population, $N_{max}$—maximum population size, $K_k$—maximal kill rate constant for bacterial population, $C_{50k}$—concentration to achieve 50% of maximal kill rate for bacterial population, H—sigmoidicity constant for bacterial population, β—maximal adaptation, and τ—rate of adaptation factor.

TABLE 5

| Parameters | Strain | |
|---|---|---|
| | PA 27853 | AB BAA 747 |
| MIC/MBC* (mg/l) | 2/2 | 4/8 |
| $K_g$ (h$^{-1}$) | 0.48 | 0.55 |
| $N_{max}$ ($10^8$ CFU/ml) | 9.80 | 6.62 |
| $K_k$ (h$^{-1}$) | 4.68 | 27.81 |
| $C_{50k}$ (mg/l) | 0.72 | 1.56 |
| H | 3.73 | 3.06 |
| β | 42.54 | 50.09 |
| τ (l/mg · h) | 0.0135 | 0.0265 |

*P. aeruginosa* susceptibility to gentamicin; *A. baumannii* susceptibility to amikacin Computer Model Prediction of Microbial Response Using the best-fit model parameter values derived, microbial response to various clinically relevant aminoglycoside exposures (fluctuating concentrations over time) over 72 hours was predicted. Two different methods were used to predict the likelihood of resistance emergence. For gentamicin, the three parallel differential equations (I-III) were used. All simulations were performed with the ADAPT II program (22). The qualitative microbial responses, with respect to resistance suppression or development, to various amikacin exposures were predicted using a 3-dimensional response surface, as described previously (25).

Hollow Fiber Infection Model

All dosing regimens investigated were guided by computer model predictions. In view of the pharmacodynamic property of gentamicin, preliminary simulations revealed that suppression of resistance would be unlikely using any clinical achievable exposures. Therefore, as a proof-of-concept, several supra-physiologic dosing regimens were investigated, in addition to 2 clinically relevant dosing regimens [Cmax/MIC of 4 dosed every 8 hours (every 8 h) and Cmax/MIC of 12 every 24 h]. Two clinically achievable dosing regimens of amikacin were examined, corresponding to Cmax/MIC of 5 every 12 h and Cmax/MIC of 20 every 24 h.

Regardless of the prediction method used, the computer simulations were compared to experimental data from an in-vitro hollow fiber infection model with similar antimicrobial agent exposures. A human-like elimination half-life (approximately 2.5 hours) for both gentamicin and amikacin was simulated in the infection models. Serial samples were obtained from the infection models over time to ascertain the simulated pharmacokinetic exposures. Aminoglycoside concentrations in these samples were assayed using validated methods as detailed below. A one-compartment linear model was fit to the observed time-concentration profiles using the ADAPT II program.

In addition, serial samples were obtained at baseline 4, 8 hours and daily (pre-dose) in duplicate from each hollow fiber system, for quantitative culture to define the effect of various drug exposures on the bacterial population. Prior to culturing the bacteria quantitatively, the bacterial samples were centrifuged at 15,000 G for 15 minutes, and reconstituted with sterile normal saline in order to minimize drug carry-over effect. Total bacterial populations were quantified by spiral plating (Spiral Biotech, Bethesda, Md.) 10× serial dilutions of the samples (50 µl) onto drug-free MHA plates. Sub-populations with reduced susceptibility (resistant) were quantified by culturing onto cation-adjusted MHA plates supplemented with the exposed agent (gentamicin or amikacin) at a concentration of 3×MIC. Since susceptibility testing is performed in twofold dilutions and 1 tube (2× in concentration) difference is commonly accepted as reasonable interday variation, quantitative cultures on drug supplemented media plates (at 3×MIC) would allow reliable detection of bacterial sub-populations with reduced susceptibility.

The media plates were incubated at 35° C. for up to 24 (total population) and 72 hours (sub-populations with reduced susceptibility), then bacterial density from each sample was enumerated visually. The theoretical lower limit of detection was 400 CFU/ml. The susceptibility of the resistant isolates (recovered from the drug-supplemented media plates at the end of the experiments) to the exposed agent was repeated to confirm the emergence of resistance.

The observed pharmacokinetic simulations in the infection models were satisfactory. Overall, the computer predictions correlated well with experimental data for both antimicrobial agents. The comparison between computer simulated and experimental bacterial responses to gentamicin are shown in FIGS. 20A-20E, respectively. A significant initial reduction in microbial burden was predicted for all gentamicin dosing regimens examined. However, regrowth over time was predicted for sub-optimal regimens (Cmax/MIC of 4 every 8 h, Cmax/MIC of 12 every 24 h, and Cmax/MIC of 36 every 24 h) with repeated dosing due to selective amplification of resistant sub-population(s). Sustained suppression of resistance emergence was achieved with an optimal dosing regimen (Cmax/MIC of 30 every 12 h).

For amikacin, a 3-dimensional surface analysis was used to predict the likelihood of resistance suppression associated with various dosing regimens (FIG. 21). The average kill rate of various dosing regimens against the most resistant bacterial sub-population was quantified by D, an index of dosing intensity. For a dosing regimen to suppress resistance amplification, it is imperative that the average kill rate is more than the intrinsic growth rate ($K_g$) of the bacterial population. As a high-throughput method to identify promising dosing regimens (combinations of dose and dosing interval) to prevent resistance development, the corresponding values of $D/K_g$ should be >1 (the region where the translucent mesh surface is above the opaque plane), as indicated by the arrow (e.g., 2000 mg; Cmax/MIC=20) given every 24 hours or 1500 mg (Cmax/MIC=15) every 12 hours]. Based on the analysis, a sub-optimal regimen (Cmax/MIC of 5 every 12 h; predicted not to prevent resistance development over time) and an optimal dosing regimen (Cmax/MIC of 20 every 24 h; predicted to suppress resistance development) were selected for prospective validation. Both the negative and positive predictive ability of the mathematical model was verified experimentally (FIG. 22).

Resistance Confirmation

Resistant isolates were recovered from drug-supplemented plates at the end of the experiments (sub-optimal dosing regimens). Both gentamicin and amikacin resistance were confirmed with repeat susceptibility testing immediately after the experiments. However, gentamicin resistance was not stable; elevated gentamicn MIC observed could not be demonstrated after serial passage on drug-free plates and storage at −70° C. This appeared to be consistent with previous in-vivo findings (26). On the other hand, amikacin resistance was phenotypically stable. Cross-resistance to gentamicin and tobramycin was observed, but not to meropenem, cefepime and levofloxacin. These data suggested that the over-expression of efflux pump (e.g., adeABC) was unlikely to be the mechanism of amikacin resistance (27).

EXAMPLE 8

In Vivo Murine Pneumonia Model

Pharmacokinetics Determination

The bacterial inoculum was prepared and inoculated into the animals as outlined below. Two hours after infection, 30 infected mice received a single dose (400 mg/kg) intra-peritoneal dose of meropenem. Investigations using lower doses (50 mg/kg and 100 mg/kg) did not result a detectable serum meropenem concentration beyond 1 hour (data not shown). However, the pharmacokinetics of higher doses of meropenem (>400 mg/kg) could not be examined due to solubility in water and the volume feasible for intra-peritoneal injection in a mouse (≦500 μl). Six mice were sacrificed by $CO_2$ asphyxiation at 0.5, 1, 1.5, 2, and 3 hours after injection. Blood samples were collected via cardiac puncture. The blood was allowed to clot on ice and centrifuged; meropenem concentrations in these serum samples were assayed by a validated method as described below. The serum concentration profiles of all the animals were analyzed by linear regression of the logarithmic-transformed data.

Mathematical Simulation of Bacterial Response

The population dynamics of *P. aeruginosa* in adapting to various meropenem concentrations was investigated previously in time-kill studies (17). To enhance the in-vitro in-vivo correlation of this study, bacterial response to meropenem was simulated mathematically. The simulations were based on the mean model parameter estimates reported previously and using the pharmacokinetics of meropenem determined above as inputs. Two scenarios with the commonly accepted optimal pharmacodynamic exposure (% T>MIC 40%) were investigated: (i) a heterogeneous population in which bacterial adaptation (reduction in overall susceptibility over time) readily occurred under a drug selective pressure; and (ii) a homogeneous population in which there was no population adaptation and the susceptibility of the population remained constant over time (the model parameter β, corresponding the maximal change in population susceptibility, was set to be zero).

Pneumonia Model Setup

Each mouse was anesthetized with a single intra-peritoneal dose (3-5 mg/kg) of tribromoethanol (Sigma, St. Louis, Mo.), and was intubated under laryngoscopic guidance. For each mouse, the correct placement of endotracheal tube was verified by placing a cooled mirror surface close to the exit to observe water vapor condensation. A few colonies of the bacterial isolates were inoculated into Ca-MHB and incubated at 35° C. until they reached late log phase growth. The bacterial suspension was diluted to the desired concentration of approximately $10^8$ CFU/ml based on absorbance at 630 nm; a mixture of wild-type and its isogenic OprD⁻ mutant in a 1000:1 ratio was used to mimic a heterogeneous bacterial population. The inocula (10 μl) were directly inoculated into the trachea of the anesthetized animals.

Two hours after infection, 3 mice were sacrificed by $CO_2$ asphyxiation to ascertain the bacterial burden in lung tissues. The lung tissues were aseptically collected and homogenized in 10 ml of sterile saline. The homogenates were centrifuged at 6000×G for 15 minutes. The supernatant was discarded and the pellets were re-suspended in normal saline to 10× their original volumes in order to minimize drug carry-over effect. They were then diluted ten-fold serially and quantitatively cultured on Mueller-Hinton agar (MHA) plates (Hardy Diagnostics, Santa Maria, Calif.) and MHA plates supplemented with meropenem at 3× the MIC of the wild-type isolate. The media plates were incubated at 35° C. in a humidified incubator for up to 24 hours (for MHA plates) and 72 hours (for meropenem-supplemented MHA plates) before reading and the bacterial burden in lung tissues enumerated.

The remaining mice were observed every 8 hours for 4 days, with or without meropenem (400 mg/kg) given intra-peritoneally every 8 hours (10 mice in each group). Total bacterial burden and those with reduced susceptibility in animal lung tissues were determined in a similar manner upon death or at the end of the experiment. Susceptibility testing was repeated on representative isolates recovered from meropenem-supplemented plates to confirm the presence of resistance.

Validity of the Pneumonia Model

A consistent bacterial burden was reliably achieved in lung tissue of the animals using the inoculation technique described above (FIG. 23). Furthermore, histopathologic examination of lung tissues 24 hours after infection revealed a massive inflammatory response and widespread invasion of gram-negative bacteria in pulmonary parenchyma (FIGS. 24A-24E), consistent with the pathophysiology of acute pneumonia in humans. Inoculation with approximately $10^6$ CFU (10 µl at $10^8$ CFU/ml) of $P.$ $aeruginosa$ resulted in 100% mortality of neutropenic animals within 24 hours in the absence of treatment. In comparison, previous investigations with 10 µl saline inoculation resulted in 0% mortality after 96 hours (data not shown).

Meropenem (400 mg/kg) resulted in a Cmax of 354.1 mg/l and a terminal elimination half-life of 19 minutes (FIG. 25). The corresponding % T>MIC for the wild-type isolate and the OprD$^-$ mutant were 33% and 26%, respectively.

Mathematical Simulation of Bacterial Response

Using an identical meropenem exposure, the simulated bacterial responses were drastically different, depending whether a heterogeneous or homogeneous population was involved (FIGS. 26A-26B). Initial decline in bacterial burden followed by regrowth, due to selective amplification of resistance sub-population, was predicted for a heterogeneous population. Sustained bacterial killing was predicted for a homogeneous population over time.

Microbiologic Response

Meropenem therapy (400 mg/kg intra-peritoneally every 8 hours) offered a significant survival benefit over 4 days, compared to placebo control (100% vs 0%, p<0.001). All dead (untreated) mice were found to have a heavier bacterial burden in lung tissues compared to baseline (FIG. 23), confirming pneumonia as the most likely cause of death in these animals. On the other hand, bacterial burden in lung tissues of (treated) mice which survived up to 96 hours revealed a bimodal distribution (FIG. 1). Complete replacement of bacterial population by the OprD$^-$ mutant in lung tissue was observed in 30% of the animals, despite the total bacterial burden in these animals was similar to baseline (FIG. 27). Repeat susceptibility testing of isolates recovered from meropenem-supplemented MHA plates did not reveal a substantial increase in MIC to meropenem or levofloxacin, compared to the OprD$^-$ mutant, suggesting that secondary mutation, e.g., efflux pump over-expression, was not evident.

The following references are cited herein:
1. Gold, H. S., and R. C. Moellering, Jr. 1996, N Engl J Med 335:1445-1453.
2. Gumbo et al. 2004, J Infect Dis 190:1642-1651
3. Jumbe et al. 2003, J Clin Invest 112:275-285.
4. Landman et al. 2002, Arch Intern Med 162:1515-1520.
5. Liu et al. 2005, Int J Antimicrob Agents 25:120-129.
6. Louie et al. 1998, Antimicrob Agents Chemother 42:1105-1109.
7. Louie et al. 2001, Antimicrob Agents Chemother 45:845-851.
8. Maglio et al. 2004, Antimicrob Agents Chemother 48:1941-1947.
9. Miyazaki et al. 2004, Antimicrob Agents Chemother 48:378-383.
10. NCCLS. 2003, Methods for dilution antimicrobial susceptibility tests for bacteria that grow aerobically; approved standard—sixth edition.
11. Neu, H. C. 1992, Science 257:1064-1073.
12. Tam et al. 2005, J Infect Dis, 192:420-428.
13. Andes, D. and Craig, W. A. 1998, Antimicrob Agents Chemother, 42:2375-2379.
14. Andes et al. 2004, Antimicrob Agents Chemother, 48:137-142.
15. Dandekar et al. 2003, J Antimicrob Chemother, 52:405-411.
16. Nicolau et al. 2000, Antimicrob Agents Chemother, 44:1291-1295.
17. Tam et al. 2005, J Antimicrob Chemother, 55:699-706.
18. Nikolaou, M. and Tam, V. H. 2006, J Math Biol, 52:154-182.
19. Weisstein, E. W. Cumulant. MathWorld—A Wolfram Web Resource, from http://mathworld.wolfram.com/Cumulant.html.
20. Tam et al. 2005, Antimicrob Agents Chemother, 49:4920-4927.
21. Giacomini et al. 1981, J Pharm Sci, 70:117-21.
22. D'Argenio, et al. 1997. ADAPT II User's Guide: Pharmacokinetic/Pharmacodynamic Systems Analysis Software. Biomedical Simulations Resource, University of Southern California, Los Angeles.
23. Mouneimne et al. 1999, Antimicrob. Agents Chemother, 43:62-66.
24. Tam et al. 2006, Antimicrob Agents Chemother, 50:2626-2631.
25. Nikolaou et al. 2007, Ann Biomed Eng, 35:1458-1470.
26. Gerber et al. 1982, J Infect Dis, 146:691-697.
27. Higgins et al. 2004, J Antimicorb Chemother, 54:821-823.
28. Leary et al. 2001), An adaptive grid non-parametric approach to pharmacokinetic and dynamic (PK/PD) models. In Fourteenth IEEE Symposium on Computer-Based Medical Systems, Bethesda, Md., 2001, pp. 289-394. IEEE Computer Society, Washington, D.C., USA.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages inherent herein. The present examples, along with the methods, procedures, systems, and/or applications described herein are presently representative of preferred embodiments, are exemplary and are not intended as limitations on the scope of the invention. Changes therein and other uses will occur to those skilled in the art which are encompassed within the spirit of the invention as defined by the scope of the claims.

What is claimed is:

1. A computer-implemented method of predicting the likelihood of a microbial population of cells associated with a pathophysiological condition of acquiring resistance to a therapeutic agent, comprising:
providing a computer-implemented simulation in a computer system including at least an input/output system and a mathematical model of growth response over a period of time of a microbial cell population in contact with a therapeutic agent, wherein the mathematical model comprises, as operably linked components:
equations for calculating in parallel and over a specified time period a rate of change of concentration of the therapeutic agent in the microbial cell population, a rate of change of cellular susceptibility to the therapeutic agent and a rate of change of burden in a surviving microbial cell population; and initial parameter values for the equations corresponding to time, infusion rate of the therapeutic agent, volume of distribution, clearance of the therapeutic agent, concentration to achieve 50% of maximal kill rate of a microbial cell population, and maximum size of a microbial cell population and constants for maximum adaptation and adaptation rate of a microbial cell population and growth rate, maximum kill rate and sigmoidicity of a microbial cell population;

inputting parameter values into the mathematical model to determine at least susceptibility of the cells to the therapeutic agent and growth of a microbial cell population during contact therewith over the period of time;

generating output values predicting cellular susceptibility and cellular growth at incremental points over the time period; and correlating, at or near the end of the time period, a decrease in cellular susceptibility output values and an increase in cell population growth values in a microbial cell population which initially demonstrated susceptibility to the therapeutic agent with the likelihood of acquisition of resistance of the microbial cell population to the therapeutic agent, thereby predicting the likelihood of acquisition of resistance to the therapeutic agent.

2. The method of claim 1, further comprising designing a dosing regimen that is pharmacologically effective against the microbial cell population based on the output values over the time period of the mathematical model.

3. The method of claim 2, further comprising compiling a library of therapeutic agents and dosing regimens effective to suppress the emergence of acquired resistance in microbial cell populations.

4. The method of claim 1, wherein the microbial cell population is a cell population of Gram negative bacteria, Gram positive bacteria, yeast, mold, mycobacteria, virus, or infectious agents used in bioterrorism.

5. The method of claim 4 wherein the microbial cell population is *Escherichia coli, Klebsiella pneumoniae, Pseudomonas aeruginosa, Streptococcus pneumoniae, Staphylococcus aureus*, HIV, avian influenza, or *Bacillus anthracis*.

6. The method of claim 1, further comprising screening a potential therapeutic agent for efficacy in suppressing resistance acquisition in one or more microbial cell populations using the computer-implemented simulation.

* * * * *